(12) United States Patent
Kashyap et al.

(10) Patent No.: US 7,697,796 B2
(45) Date of Patent: Apr. 13, 2010

(54) PLASMON-POLARITON REFRACTIVE-INDEX FIBER BIO-SENSOR WITH FIBER BRAGG GRATING

(75) Inventors: Raman Kashyap, Baie D'Urfé (CA); Vincent Treanton, Cremieu (FR); Lutfu Celebi Ozcan, Saint Laurent (CA)

(73) Assignee: Corporation De L'Ecole Polytechnique De Montreal, Montreal (CA)

( * ) Notice: Subject to any disclaimer, the term of this patent is extended or adjusted under 35 U.S.C. 154(b) by 0 days.

(21) Appl. No.: 11/914,637

(22) PCT Filed: May 15, 2006

(86) PCT No.: PCT/CA2006/000787

§ 371 (c)(1),
(2), (4) Date: May 29, 2008

(87) PCT Pub. No.: WO2006/122402

PCT Pub. Date: Nov. 23, 2006

(65) Prior Publication Data

US 2008/0267555 A1    Oct. 30, 2008

(51) Int. Cl.
*G02B 6/00* (2006.01)
*G02B 6/02* (2006.01)

(52) U.S. Cl. .................... 385/12; 385/13; 385/125

(58) Field of Classification Search .................. 385/12, 385/13, 125
See application file for complete search history.

(56) References Cited

U.S. PATENT DOCUMENTS

| 7,212,692 | B2 * | 5/2007 | Yan .............................. 385/12 |
| 7,541,573 | B2 * | 6/2009 | Emmerson et al. ............ 385/12 |
| 2005/0018949 | A1 | 1/2005 | Yan |

FOREIGN PATENT DOCUMENTS

EP    1300675    4/2003

OTHER PUBLICATIONS

James et al., "Optical Fibre Long-Period Grating Sensors: Characteristics and Application," Institute of Physics Publishing-Measurement Science and Technology, No. 14, Mar. 2003, R49-R61.

(Continued)

*Primary Examiner*—Charlie Peng
(74) *Attorney, Agent, or Firm*—Fay Kaplun & Marcin, LLP

(57) ABSTRACT

An optical waveguide sensing method and device in which a waveguide layer receives an optical signal and propagates the optical signal in accordance with a predetermined optical waveguide propagation mode. A testing medium surface in communication with the waveguide layer is responsive to a testing medium for modifying at least one characteristic of the propagated optical signal in relation to a given parameter of the testing medium. In this manner, the modified characteristic of the propagated optical signal can be measured in view of determining the given parameter of the testing medium.

26 Claims, 11 Drawing Sheets

OTHER PUBLICATIONS

Jette-Charbonneau et al., "Bragg Gratings Based on Long-Range Surface Plasmon-Polariton Waveguides: Comparison of Theory and Experiment," IEEE Journal of Quantum Electronics, vol. 41, No. 12, Dec. 2005, pp. 1480-1491.

Jorgenson et al., "A Fiber-Optical Chemical Sensor Based on Surface Plasmon Resonance", Sens. Actuators B., vol. 12, pp. 213-320, 1993.

Ronot-Trioli et al., "Fiber Optic Chemical Sensor Based on Surface Plasmon Monochromatic Excitation", Anal. Chim. Acta., vol. 319, pp. 121-127, 1996.

Ronot-Triolli et al., "Monochromactic Excitation of Surface Plasmon Resonance in an Optical-Fiber Refractive-Index Sensor", Sens. Actuators A., vol. 54, pp. 589-593, 1996.

Lin et al., "The Effects of Polarization of the Incident Light-Modeling and Analysis of a SPR Multimode Optical Fiber Sensor", Sens. Actuators A., vol. 84, pp. 198-204, 2000.

Januts et al., "Excitation and Superfocusing of Surface Plasmon Polaritons on a Silver-Coated Optical Fiber Tip", Opt. Comm., vol. 253, pp. 118-124, 2005.

Gupta et al. "Sensitivity Evaluation of a Multi-Layered Surface Plasmon Resonance-Based Fiber Optical Sensor: A Theoretical Study", Sens. Actuators B., vol. 107, pp. 40-46, 2005.

Iga et al. "Hetero-Core Structured Fiber Optical Surface Plasmon Resonance Sensor with Silver Film", Sens. Actuators B., vol. 101, pp. 368-372, 2004.

Trouillet, et al. "Chemical Sensing by Surface Plasmon Resonance in a Multimode Optical Fiber", Pure Appl. Opt., vol. 5, pp. 227-237, 1996.

Homola et al., "Surface Plasmon Resonance Sensors: Review", Sens. Actuators B., vol. 54, pp. 3-15, 1999.

Khosravi et al., "Surface Polaritons in Cylindrical Optical Fibers", J. Opt. Soc. Am., A., vol. 8, pp. 112-122, 1991.

Erdogan "Cladding-Mode Resonances in Short-and Long-Period Fiber Grating Filters", J. Opt. Soc. Am. A., vol. 14, pp. 1760-1773, 1997.

Erdogan "Fiber Grating Spectra", J. Lightware Technol., vol. 15, pp. 1277-1294, 1997.

Nemova et al. "Fiber Bragg Grating Assisted Surface Plasmon-Polaritons Sensor", Pot. Lett, (In Press), Jul. 15, 2006, vol. 31, No. 14, pp. 2118-2120.

\* cited by examiner

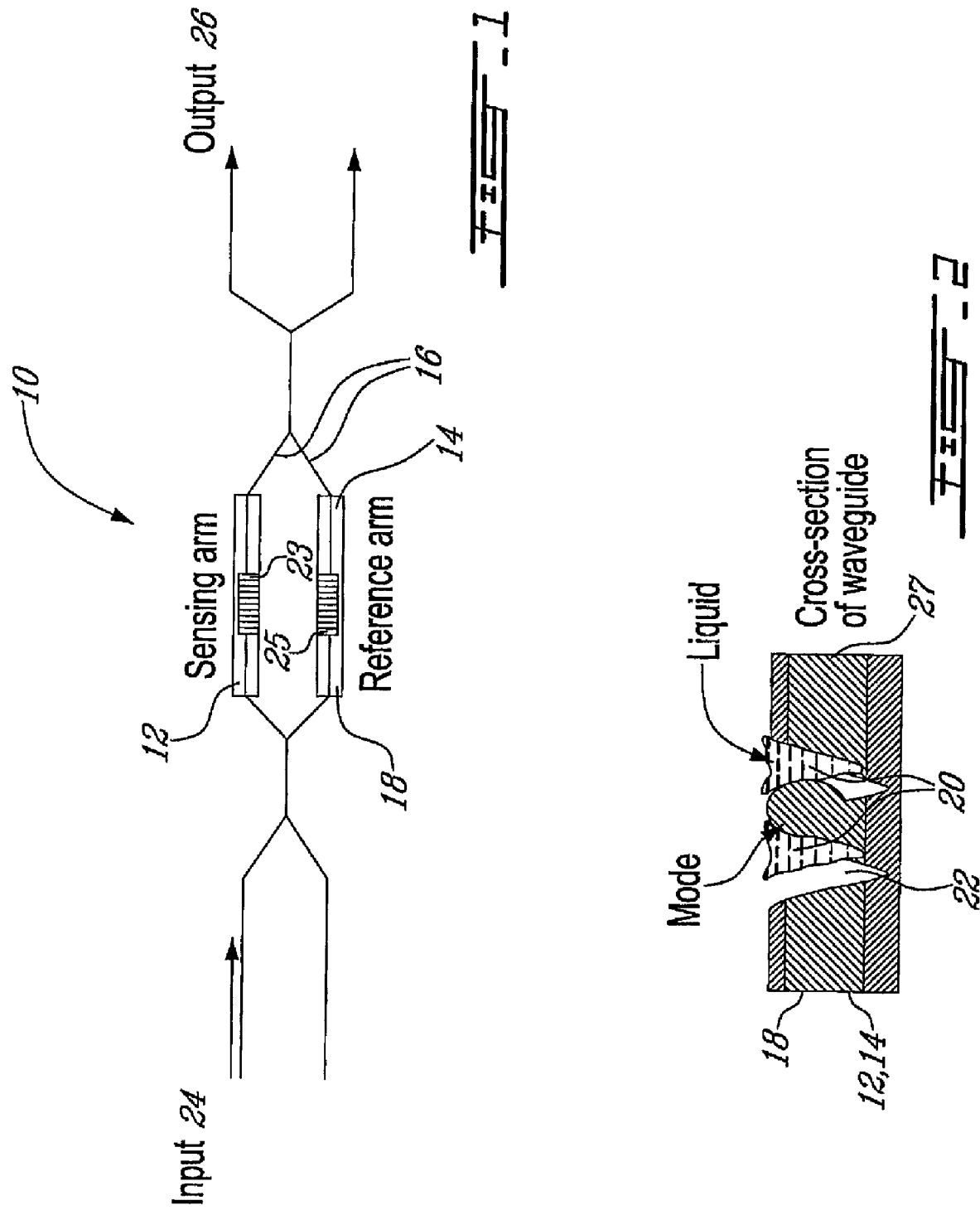

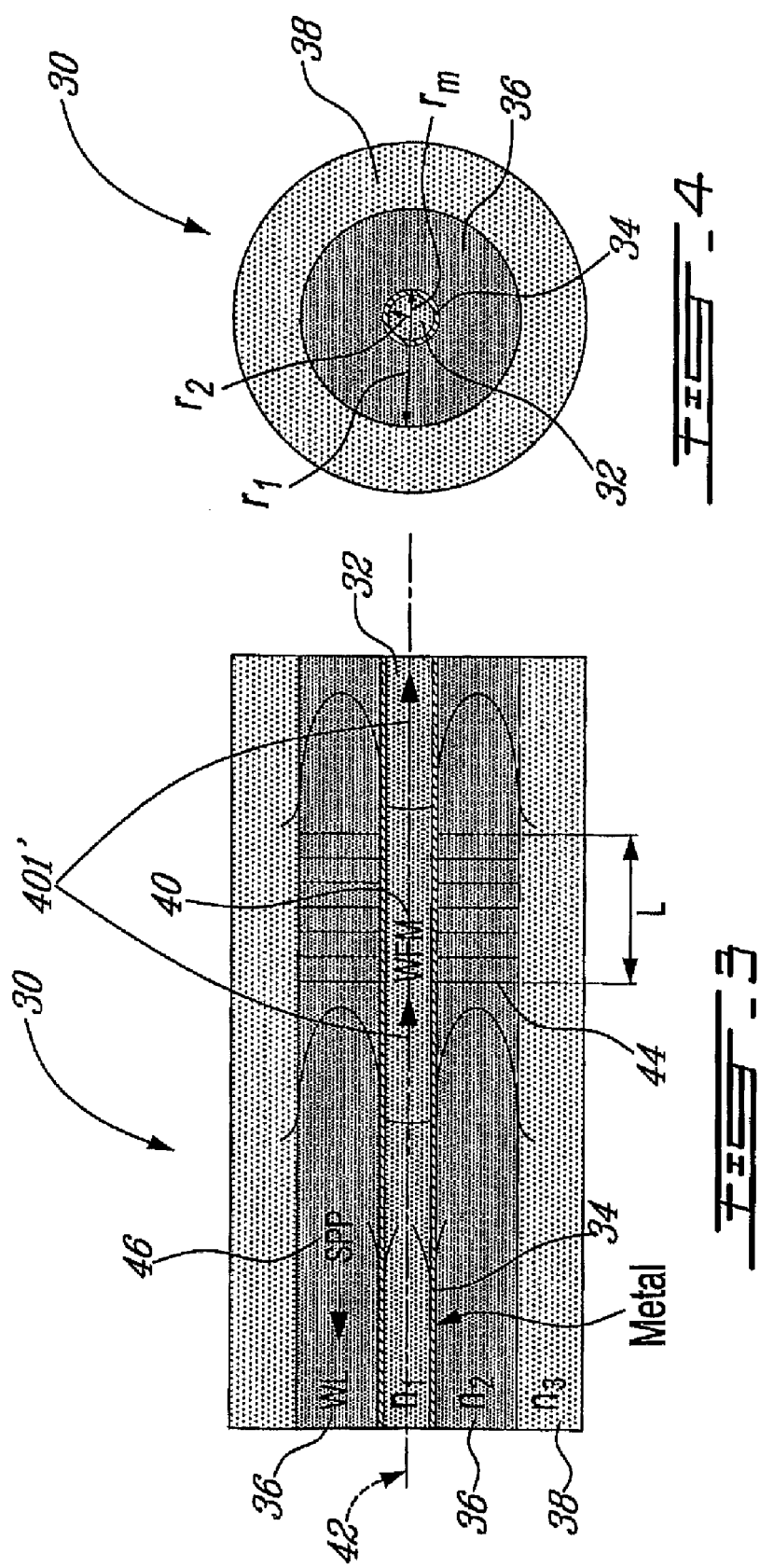

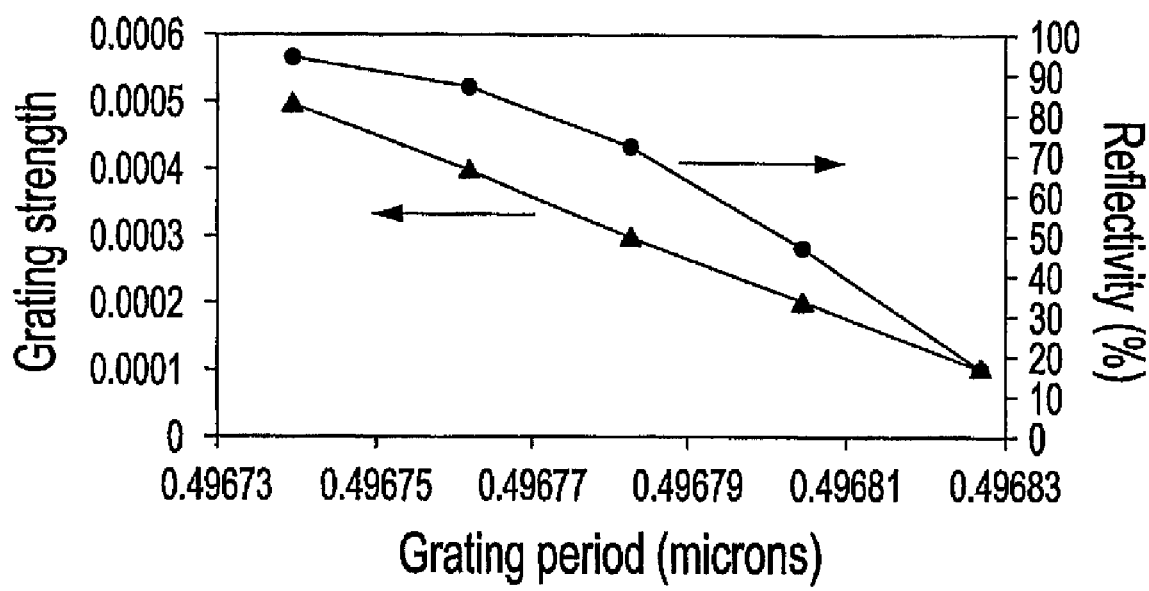
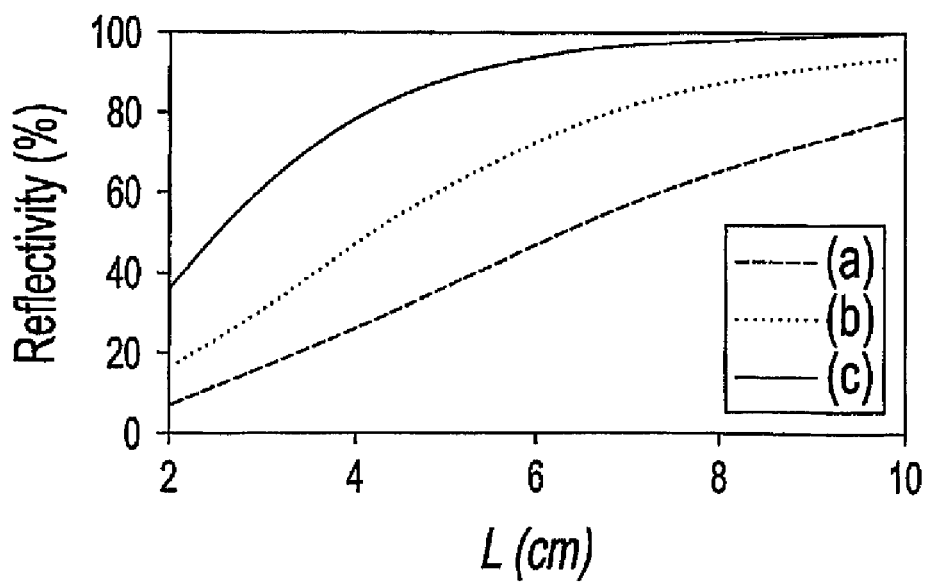
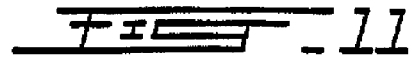

PLASMON-POLARITON REFRACTIVE-INDEX FIBER BIO-SENSOR WITH FIBER BRAGG GRATING

FIELD OF THE INVENTION

The present invention generally relates to sensors, in particular but not exclusively to plasmon-polariton refractive-index fiber bio-sensors with fiber Bragg grating.

BACKGROUND OF THE INVENTION

Bio-sensing is usually performed by measuring a parameter such as the refractive index of a liquid which is dependent on the concentration of a solute measurand. Conventional methods require an absolute measurement of the refractive index detected through a change in transmission properties, for example the Surface Plasmon Resonance angle. Such measurement can be quite difficult to implement and requires a lot of equipments generally complicated to use. An optical fiber-based interferometer may be used but the core region of the fiber(s) is difficult to access since it is completely enclosed; such an interferometer is very unstable due to the nature of the fiber.

A Surface Plasmon-Polariton (SPP) represents a surface electromagnetic wave that propagates between two media having respective permittivity real parts of opposite signs and made, for example, of respective dielectric and metallic materials [1]. SPP can be supported on cylindrical and planar surfaces or geometries. The SPP field components have their maxima at the interface between the media and the metal layer and decay exponentially in both media [1]. Their small penetration depth in the media makes SPPs a great tool for sensor applications.

Traditional planar SPP sensor systems used for bio-sensing work on the principle of prism coupling by altering the angle of the incident beam to match the propagation constant of the SPP. This relies on incorporating moving parts into the sensor.

Other known optical fiber sensors are based on the properties of the SPP penetrating along the surface of a thin gold or silver layer deposited on an exposed portion of the core of the optical fiber [2-10]. In the latter optical fiber sensors, the core of the fiber is used instead of the coupling prism of the traditional planar SPP sensor systems. More specifically, these fiber sensors are constructed by modifying traditional SPP planar sensor systems. Scanning the light wavelength or change in the angle of incidence of the incident light is used for SPP excitation. Generally, the resulting optical fiber sensors include moving parts which render the SPP excitation process rather difficult.

Therefore, there is a need for an improved optical fiber sensor using SPP, which is simple, free from instability and demonstrates a high efficiency whereby it can be used as a successful bio-sensor.

SUMMARY OF THE INVENTION

More specifically, in accordance with the present invention, there is provided an optical waveguide sensing device comprising: a waveguide layer for receiving an optical signal and propagating the optical signal in accordance with a predetermined optical waveguide propagation mode; and a testing medium surface in communication with the waveguide layer and responsive to a testing medium for modifying at least one characteristic of the propagated optical signal in relation to a given parameter of the testing medium. Therefore, the modified characteristic of the propagated optical signal can be measured in view of determining the given parameter of the testing medium.

The present invention also relates to an optical waveguide sensing method comprising: receiving an optical signal and propagating said optical signal through a waveguide layer in accordance with a predetermined optical waveguide propagation mode; applying a testing medium to a testing medium surface in communication with the waveguide layer; and modifying at least one characteristic of the propagated optical signal in relation to a given parameter of the testing medium. Therefore, the modified characteristic of the propagated optical signal can be measured in view of determining the given parameter of the testing medium.

The foregoing and other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

In the appended drawings:

FIG. 1 is a schematic view of a measuring device comprising an optical fiber waveguide sensor according to a first illustrative embodiment of the present invention, for measuring liquids;

FIG. 2 is a cross sectional view of the optical fiber waveguide sensor of FIG. 1;

FIG. 3 is a schematic side view of an optical fiber waveguide sensor according to a second illustrative embodiment of the present invention;

FIG. 4 is schematic end view of the optical fiber waveguide sensor of FIG. 3;

FIG. 10 is a graph showing the dependence between a grating period $\Lambda$ and a grating amplitude or strength $\sigma$ (left axis), and the dependence between the grating period $\Lambda$ and a grating reflectivity R (right axis) for a grating length L=6 cm and a thickness of the metal layer $\Delta$=100 Å;

FIG. 11 is a graph showing the dependence between the grating length L and the grating reflectivity R with $\Delta$=100 Å and (a) $\sigma=2\times10^{-4}$, $\Lambda$=496.8 nm, (b) $\sigma=3\times10^{-4}$, $\Lambda$=496.78 nm, (c) $\sigma=5\times10^{-4}$, $\Lambda$=496.74 nm;

Figure 18:
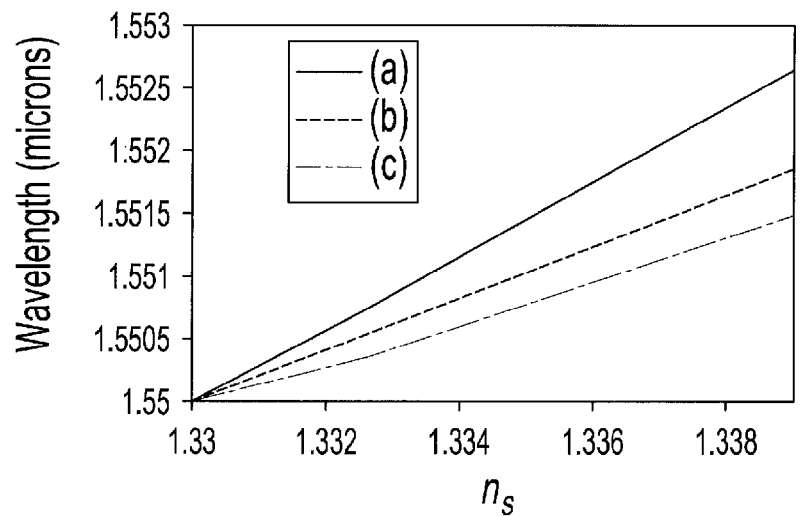
FIG. 18 is a graph of the wavelength corresponding to the maximum of the grating reflectivity R (70%) versus the refractive index $n_s$ of the surrounding medium for (a) $\Delta=100$ Å, L=9 cm, $\Lambda=420$ nm, $\sigma$(or GS)=$4\times10^{-4}$; (b) $\Delta=130$ Å, L=5 cm, $\Lambda=469$ nm, $\sigma$(or GS)=$2\times10^{-4}$; and (c) $\Delta=150$ Å, L=4 cm, $\Lambda=496$ nm, $\sigma$(or GS)=$10^{-4}$.

The following Table 1 shows the parameters used in FIG. 18:

TABLE I

| Wavelength shift per $10^{-3}$ change in the refractive index, n | $\Delta$, Å | L, cm | GS | $\Lambda$, nm | R % |
|---|---|---|---|---|---|
| ~300 pm | 100 | 9 | $4\times10^4$ | 420 | 70 |
| ~190 pm | 130 | 5 | $2\times10^4$ | 477 | 70 |
| ~150 pm | 150 | 4 | $1\times10^4$ | 496 | 70 |

DETAILED DESCRIPTION

According to a first illustrative embodiment of the present invention, a bio-sensor set-up of the interferometric type is illustrated in FIG. 1. The bio-sensor set-up of FIG. 1 comprises a bio-sensor 10 having first and second optical paths of an optical interferometer 16 (Mach-Zehnder Interferometer (MZI), Michelson interferometer, etc.). FIG. 1 illustrates, as a non-limitative example, a MZI 16 fabricated from optical waveguide sensors such as 18. The MZI 16 comprises an optical waveguide sensor 18 for each optical path, an input 24 and an output 26. The first optical path comprises a first optical waveguide sensor 18 defining a sensing arm 12 and the second optical path comprises a second optical waveguide sensor 18 defining a reference arm 14.

The general principle of the bio-sensor set-up of FIG. 1 is the following. The input 24 normally consists of an optical signal supplied to both the sensing arm 12 and the reference arm 14. The introduction of a liquid 20 (FIG. 2), whose parameter such as the refractive index needs to be measured, in the sensing arm 12 changes the optical propagation characteristics of the optical path corresponding to that arm 12 compared to those of the reference arm 14. Usually, the sensing arm 12 and the reference arm 14 are, if not identical, very similar. Since the first and second paths are in very close proximity with respect to each other, a change, for example a phase or attenuation change, can be detected in the optical signal at the output 26 and this change can be converted to a change or value of the parameter of the liquid to be detected such as the refractive index.

As illustrated in FIG. 2, the optical waveguide sensors 18 (sensing arm 12 and reference arm 14) are formed with a number, for example two or more longitudinal trenches 22 extending through the optical waveguide layer 27. The longitudinal trenches 22 allow the liquid 20 to be easily introduced into the first optical path (sensing arm 12). The liquid 20 is then in contact with the surface of the trenches and therefore with the optical waveguide layer 27. Introduction of the liquid 20 into the trenches 22 will change the refractive index of the medium into the trenches 22 and therefore will change the optical propagation characteristics of the optical waveguide sensor 30. As a consequence, this will also alter the phase or attenuation of the optical signal propagated through the optical waveguide sensor 18.

The optical interferometer 16 is small (cms long) and is fabricated on a chip (integrated circuit). Therefore, the optical interferometer 16 is a very stable platform. Introduction of the liquid 20 into the trenches such as 22 of the sensing arm 12 can be referenced by introduction of a reference solution into the trenches 22 of the reference arm 14. A temperature stable, highly sensitive interferometer 16 is thereby produced. Refractive index changes as low as $10^{-7}$ can be detected in such a self-referencing interferometer system, something which is very difficult to attain any other way.

Optionally, two identical Bragg gratings 23 and 25 can be produced in corresponding regions of the sensing 12 and reference 14 arms, respectively. These Bragg gratings 23 and 25 cause the propagated optical signal on the output 26 to be highly sensitive to any difference between the sensing arm 12 and reference arm 14 by shifting the Bragg wavelength of the affected optical waveguide sensor 18 (sensing arm 12) (see "Raman Kashyap, Fiber Bragg Gratings, Academic Press, 1999, Section 6.3"). In this manner, the light reflection and transmission characteristics of the interferometer 16 change as a function of the refractive index of the liquid 20 introduced into the trenches 22 of the waveguide sensors 18.

The simple set-up of FIG. 1 enables easy introduction and removal of liquid 20 into and from the trenches 22 of the bio-sensor 10, e.g. blood or other bodily fluids for example to conduct sugar analysis, potassium content, etc. As described hereinabove, this will also allow the bio-sensor to measure a change from an ambient reference. As the optical waveguide sensor 18 is accessible from the outside, it is very easy to clean, disinfect and otherwise maintain.

FIGS. 3 and 4 illustrate a second non-restrictive illustrative embodiment of an optical fiber waveguide sensor 30 that can be used, for example, as optical waveguide sensors 18 in the bio-sensor 10 of FIG. 1. More specifically, the optical fiber waveguide sensor 30 presents the general configuration of a modified optical fiber.

Figure 6:
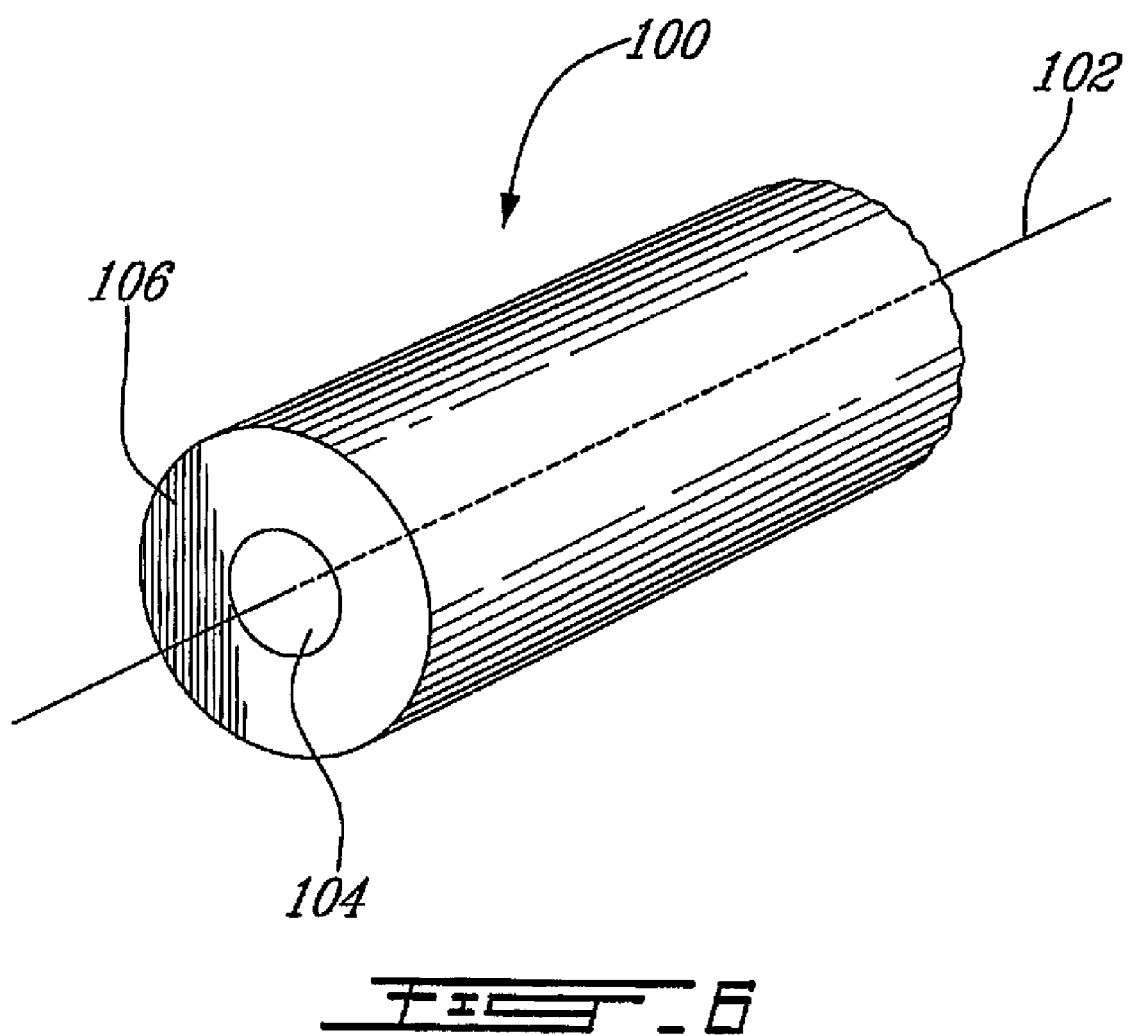
FIG. 6 is a perspective view of a classical fiber having multiple layers.

Before describing the optical fiber waveguide sensor 30, characterization of a classical optical fiber 100 will be reviewed. FIG. 6 shows the structure of such a classical fiber 100. More specifically, a classical optical fiber 100 is generally a dielectric waveguide of a generally cylindrical shape that transmits light along its longitudinal axis 102 through total internal reflection. A classical optical fiber 100 consists of a plurality of superposed layers including a central cylindrical core layer 104 surrounded by a tubular cladding layer 106. For total internal reflection to confine the optical signal inside the core layer 104, the refractive index of the core layer 104 must be greater than the refractive index of the cladding layer 106. The boundary between the core layer 104 and cladding layer 106 may either be abrupt such as in step-index optical fiber or gradual such as in graded-index optical fiber.

Any dielectric layer in a multi-layer optical fiber 100 will be considered as a waveguided layer (WL) if its refractive index is higher than the refractive indexes of all the other dielectric fiber layers. Therefore, the WL is generally the core layer 104.

As illustrated in FIG. 3, the optical fiber waveguide sensor 30 can be used, for example, in the MZI 16 of FIG. 1 as the sensing 12 and reference 14 arms. The optical fiber waveguide sensor 30 is generally of a cylindrical shape and is made of many superposed layers. At the center region of the optical fiber waveguide sensor 30 is placed a testing medium 32 which can be the liquid 20 of FIG. 2. The testing medium 32 has a radius $r_1$ and a refractive index $n_1$. Surrounding the testing medium 32 is a cylindrical layer of metal 34 having a certain thickness $\Delta = (r_m - r_1)$, where $r_m$ is the larger radius of the cylindrical metal layer 34. Then comes a WL 36 having a larger radius $r_2$ and a refractive index $n_2$. Finally the last outer layer consists of a cladding layer 38 with a refractive index $n_3$.

The electromagnetic wave oscillating in the WL 36 and exponentially decaying in all the other fiber layers is called the Waveguided Fiber Mode (WFM) 40. The WFM 40 propagates along the longitudinal axis 42 of the optical fiber waveguide sensor 30 in a forward direction (see arrows 401).

A SPG 44 (Short-Period fiber Bragg Grating) can be imprinted in the WL 36. Fiber Bragg gratings have shown significant potential for mode coupling in optical fibers. The SPG 44 can be viewed as a reflective mirror, in which a forward-propagation WFM 40 can be coupled to a backward-propagation SPP 46. Therefore, the direction of propagation of the SPP 46 is opposite of the direction of propagation of the WFM 40. Also, the SPG 44 is designed in such a way that the resonance or excitation coupling between the WFM 40 and the SPP 46 is the most efficient. For that purpose, the SPG 44 has a length L and grating parameters such as a grating period $\Lambda$, a grating amplitude or strength $\sigma$ and a grating reflectivity R that can all be adjusted.

The SPP 46 can propagate at the interface of a dielectric and metal media. The SPP 46 has an electrical field component E and a magnetic field component H having their maxima at the interface between the metal layer 34 and the medium 32 and the interface between the metal layer 34 and the WL 36 and decay exponentially into both the medium 32 and the WL 36 as shown in FIG. 3. This small penetration depth in the medium 32 makes the SPP highly suitable for refractive index sensing of the testing medium 32.

The principle of operation of the optical fiber waveguide sensor 30 is based on the efficient energy transfer between the WFM 40 and the SPP 46 provided by properly designing the SPG 44 imprinted into the WL 36. More specifically, the excitation of the SPP 46 is based on the resonance coupling between the WFM 40 and the SPP 46 as provided by the SPG 44. Furthermore, the efficiency of the SPP excitation as a function of the reflectivity R of the SPG 44 was determined on the basis of well developed coupled-mode theory for fiber Bragg gratings as described in details in a number of references [7-9, 11].

Waveguided Fiber Mode (WFM)

Fiber modes as well as SPPs such as 46 are solutions of Maxwell's equations with standard boundary conditions at the fiber surface layers. The above described optical fiber waveguide sensor 30 comprises the cylindrical layered structure of FIGS. 3 and 4. Cylindrical polar coordinates $(r, \theta, z)$ are used to describe the cylindrical layered optical fiber waveguide sensor 30. The region $r < r_1$ is occupied by the testing medium 32 with a refractive index $n_1$. The region $r_1 < r < r_m$ comprises the metal layer 34 supporting a plasmon-polariton (SPP). The permittivity $\in(\omega)$ of the metal layer 34 at a certain frequency $\omega$ is modeled by the Drude formula as follows:

$$\in(\omega) = \in_\infty [1 - \omega_p^2 / \omega(\omega + i\lceil)]$$

where $\in_\infty$ is a high-frequency value of $\in(\omega)$, $\omega_p$ is a plasma frequency, $\lceil$ is a damping rate of the plasma and i is $\sqrt{-1}$. The metal layer 34 is deposited on the inner cylindrical face of the WL 36, as illustrated in FIGS. 3 and 4. The WL 36 has a refractive index $n_2$ and occupies the region $r_m < r < r_2$. The WL 36 is covered by the cladding layer 38 with a refractive index $n_3$ in the region $r > r_2$. The conditions $n_2 > n_1$ and $n_2 > n_3$ are imposed on the layered optical fiber waveguide sensor 30. The dependence on $z$, $\theta$, and time $t$ is taken into account by means of second derivatives $\partial^2/\partial z^2$, $\partial^2/\partial \theta^2$, and $\partial^2/\partial t^2$, so solutions are sought in which all field components contain a common factor $\exp(i\beta_{v\mu}^{f,p} z + i v\theta - i\omega t)$, where $\beta_{v\mu}^{f,p}$ is a propagation constant, superscripts f and p correspond to the WFM 40 and the SPP 46, respectively, and the variable v represents an azimuth mode number. It should be noted that in the case of cylindrical geometries, except in the special case where $v=0$, the propagation modes do not have pure transverse electric field component $\overline{E}$ and/or magnetic field component $\overline{H}$.

Each layer of the optical fiber waveguide sensor 30 is characterized by its phase parameters:

$$u_i^2 = -w_i^2 = k_0^2 n_i^2 - (\beta_{v\mu}^{f,p})^2 \quad (1)$$

where $k_0$ is the vacuum wave-number, $n_i$ is the refractive index of the $i^{th}$-layer of the optical fiber waveguide sensor 30, with $i = 1, 2, 3$ or m (the metal layer 34). The electric field components of the propagation modes of the cylindrical layered optical fiber waveguide sensor 30 involve Bessel functions of the real argument, which are oscillatory in character, for $u_i^2 > 0$ and Bessel functions of imaginary argument, which are asymptotically exponential, for $w_i^2 > 0$. Generally, non-radiative propagation modes of the cylindrical optical fiber waveguide sensor 30 are considered as well for the following regions: the cladding layer 38 ($r > r_2$), the testing medium 32 ($0 < r < r_1$), and the metal layer 34 ($r_1 < r < r_m$). The electric field components of the propagation modes of the cylindrical layered optical fiber waveguide sensor 30 are in the form of:

$$E_\phi = -C_1^{f,p_1} w_1 I'_v(w_1 r) - A_1^{f,p} \frac{\sigma_2}{r n_1^2} I_v(w_1 r), \quad (2)$$

$$E_z = -A_1^{f,p} w_1^2 \frac{\sigma_2}{v \beta_{v\mu}^f n_1^2} I_v(w_1 r),$$

for the testing medium 32 ($0 < r < r_1$), $$E_\phi = -w_m (C_m^{f,p} I'_v(w_m r) + D_m^{f,p} K'_v(w_m r)) - \quad (3)$$

$$\frac{\sigma_2}{r \varepsilon(\omega)} (A_m^{f,p} I_v(w_m r) + B_m^{f,p} K_v(w_m r)),$$

$$E_z = -\frac{w_m^2 \sigma_2}{\varepsilon(\omega) v \beta_{v\mu}^f} (A_m^{f,p} I_v(w_m r) + B_m^{f,p} K_v(w_m r)),$$

for the metal layer 34 ($r_1 < r < r_m$), $$E_\phi = -u_2(C_2^f J_\nu'(u_2 r) + D_2^f Y_\nu'(u_2 r)) - \frac{\sigma_2}{r n_2^2}(A_2^f J_\nu(u_2 r) + B_2^f Y_\nu(u_2 r)), \quad (4)$$

$$E_z = \frac{u_2^2 \sigma_2}{n_2^2 \nu \beta_{\nu\mu}^f}(A_2^f J_\nu(u_2 r) + B_2^f Y_\nu(u_2 r)),$$

for the WL 36 ($r_m < r < r_2$); and $$E_\phi = -D_3^{f,p} w_3 K_\nu'(w_3 r) - B_3^{f,p} \frac{\sigma_2}{r n_3^2} K_\nu(w_3 r), \quad (5)$$

$$E_z = -B_3^{f,p} \frac{w_3^2 \sigma_2}{n_3^2 \nu \beta_{\nu\mu}^f} K_\nu(w_3 r),$$

for the cladding layer 38 ($r > r_2$), where $\sigma_2 = i\nu n_{\nu\mu} Z_0$, and $Z_0 = 377\Omega$ is the electromagnetic impedance in vacuum. $n_{\nu\mu}^f = \beta_{\nu\mu}^f / k_0$ is the normalized propagation constant of the WFM 40. Subscript μ is used to distinguish the different solutions of the dispersion relation for a given azimuth mode number ν.

The magnetic field components of the propagation modes $H_z$ and $H_\phi$ can be obtained on the basis of the relations presented in reference [11] for standard fiber core modes. The values $A_1^f$, $C_1^f$, $A_l^f$, $B_l^f$, $C_l^f$, $D_l^f$, (l=m, 2), and $B_3^f$, $D_3^f$ are arbitrary constants, which can be calculated from the continuity of the $E_z$, $H_z$, $E_\phi$ and $H_\phi$ components on the layer's boundaries and from the condition that the power carried by each propagation mode is normalized to 1 Watt. $J_\nu$ and $Y_\nu$ are the Bessel function of the first and second kinds of order ν, respectively. $I_\nu$ and $K_\nu$ are the modified Bessel function of the first and second kinds of order ν, respectively. The primes over these functions indicate the first derivative. The dispersion relation for cylindrical layered optical fiber waveguide sensors 30 can be obtained on the basis of the continuity conditions for the electric and magnetic components on layers' boundaries. Using the above mentioned equation (1):

$$u_i^2 = -w_i^2 = k_0^2 n_i^2 - (\beta_{\nu\mu}^{f,p})^2$$

it is possible to find the region where $n_{\nu\mu}^f$ as a solution of the dispersion relation is given by:

$$\max(n_1, n_3) < n_{\nu\mu}^f < n_2. \quad (6)$$

Generally speaking, the case of the single mode solution is considered, since it is free from the intermodal interference; this condition is used for the interrogation unit (not shown) monitoring the transmitted WFM 40 at the output 26 of the bio-sensing set-up of FIG. 1.

Surface Plasmon-Polariton (SPP)

As mentioned in the foregoing description, the electric and magnetic field components of the SPP 46 have their maxima at the interface between the metal layer 34 and the medium 32 and the interface between the metal layer 34 and the WL 36 and decay exponentially into both the medium 32 and the WL 36. In contrast to a hybrid WFM 40, which will be discussed hereinafter, a "pure" SPP 46 of the multi-layered optical fiber waveguide sensor 30 has maxima at the above mentioned interfaces and decay exponentially in all the others layers of the optical fiber waveguide sensor 30, including the WL 36.

For a theoretical description of the electric field component of a "pure" SPP 46, the term $\beta_{\nu\mu}^f$ needs to be formally replaced by $\beta_{\nu\mu}^p$ and the constants $A_1^p$, $C_1^p$, $A_m^p$, $B_m^p$, $C_m^p$, $D_m^p$, $B_3^p$, $D_3^p$ should be used instead of the values $A_1^f$, $C_1^f$, $A_m^f$, $B_m^f$, $C_m^f$, $D_m^f$, $B_3^f$, $D_3^f$ in the above equations (2), (3), (5). Also, the expression (4), describing the oscillating electric field components in the WL 36, is replaced by a new expression describing the decay components of the electric field in this layer. The electric field components of the "pure" SPP 46 in the WL 36 present the form of:

$$E_\phi = -w_2(C_2^p I_\nu'(w_2 r) + D_2^p K_\nu'(w_2 r)) - \frac{\sigma_2}{r n_2^2}(A_2^p I_\nu(w_2 r) + B_2^p K_\nu(w_2 r)), \quad (7)$$

$$E_z = \frac{-w_2^2 \sigma_2}{n_2^2 \nu \beta_{\nu\mu}^f}(A_2^p I_\nu(w_2 r) + B_2^p K_\nu(w_2 r)),$$

where $r_m < r < r_2$.

The values $A_1^p$, $C_1^p$, $A_l^p$, $B_l^p$, $C_l^p$, $D_l^p$, (l=m, 2), and $B_3^p$, $D_3^p$, like in the case of the WFM 40, can be calculated from the continuity of the $E_z$, $H_z$, $E_\phi$, and $H_\phi$ electric and magnetic field components on the layers' boundaries and from the condition that the power carried by each "pure" SPP 46 is normalized to 1 Watt.

The dispersion relation for a "pure" SPP 46 can be obtained in the same way as the dispersion relation for the WFM 40, that is on the basis of the continuity conditions for the electric and magnetic field components on the layers' boundaries, but the expression (4) for the electric field components in the layer $r_m < r < r_2$ needs to be replaced by the expression (7). In accordance with equation (1) the normalized propagation constant $n_{11}^p$ of the "pure" SPP 46 can be found as a solution of the dispersion relation in the interval:

$$n_{11}^p > n_2. \quad (8)$$

For the sake of simplicity, in the following description, the "pure" SPP 46 will be designated as the SPP 46 of the cylindrical multi-layered optical fiber waveguide sensor 30.

Figure 7:
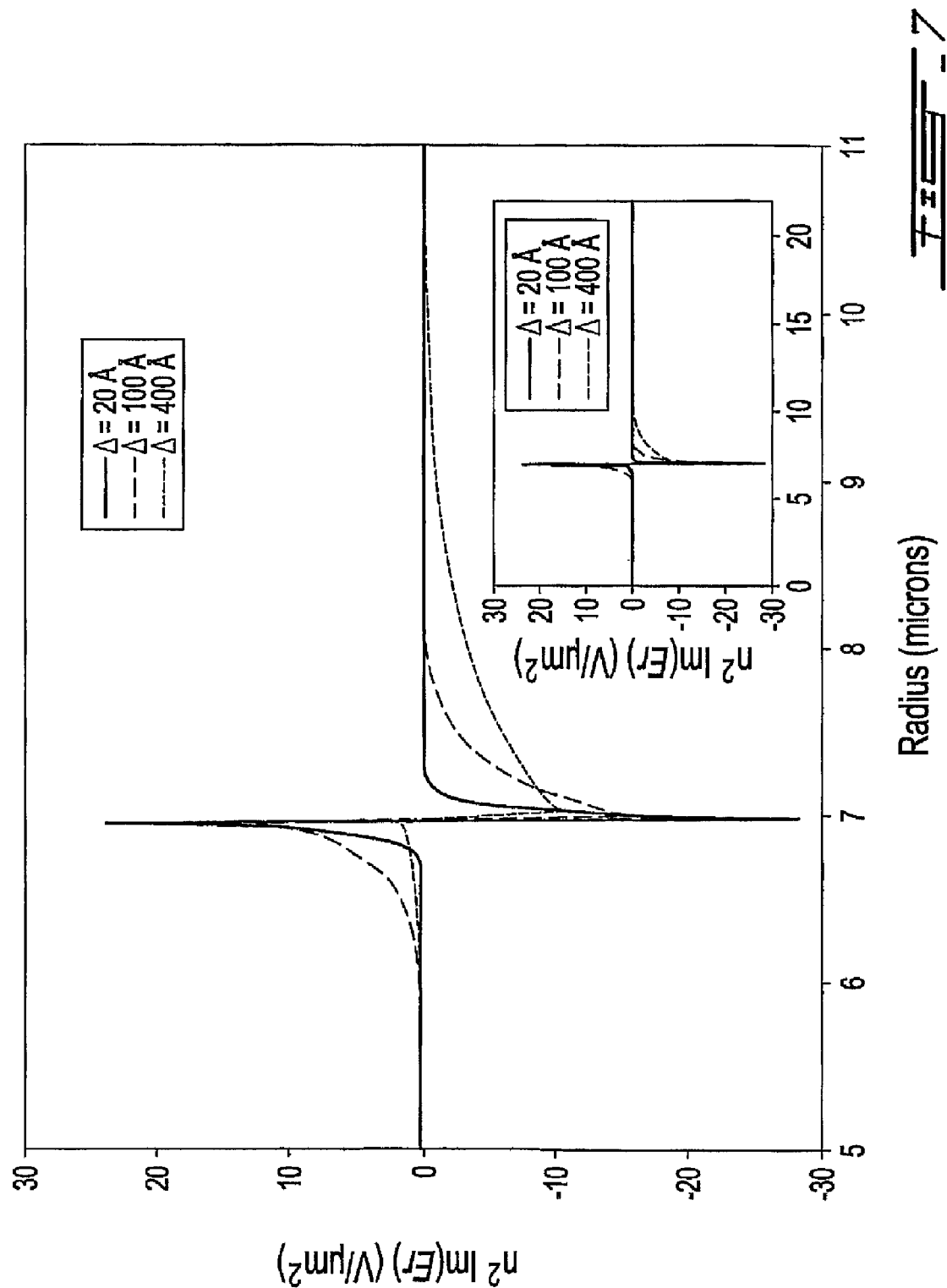
FIG. 7 is a plot of the radial component of the electric field of the SPP times the $n^2(r)$ for structures with different metal layer thicknesses $\Delta$ in the vicinity of the metal layer.

FIG. 7 is a plot of the radial component of the electric field of the SPP 46 times the $n^2(r)$ for different thicknesses Δ of the metal layer 34 in the vicinity of this metal layer 34. The inset in FIG. 7 shows the same dependence for the whole multi-layered optical fiber waveguide sensor 30. When the metal layer 34 becomes thinner the SPP 46 is more confined to the vicinity of the metal layer 34. In other words, by reducing the thickness Δ of the metal layer 34, the sensitivity of the cylindrical multi-layered optical fiber waveguide sensor 30 is increased.

Figure 8:
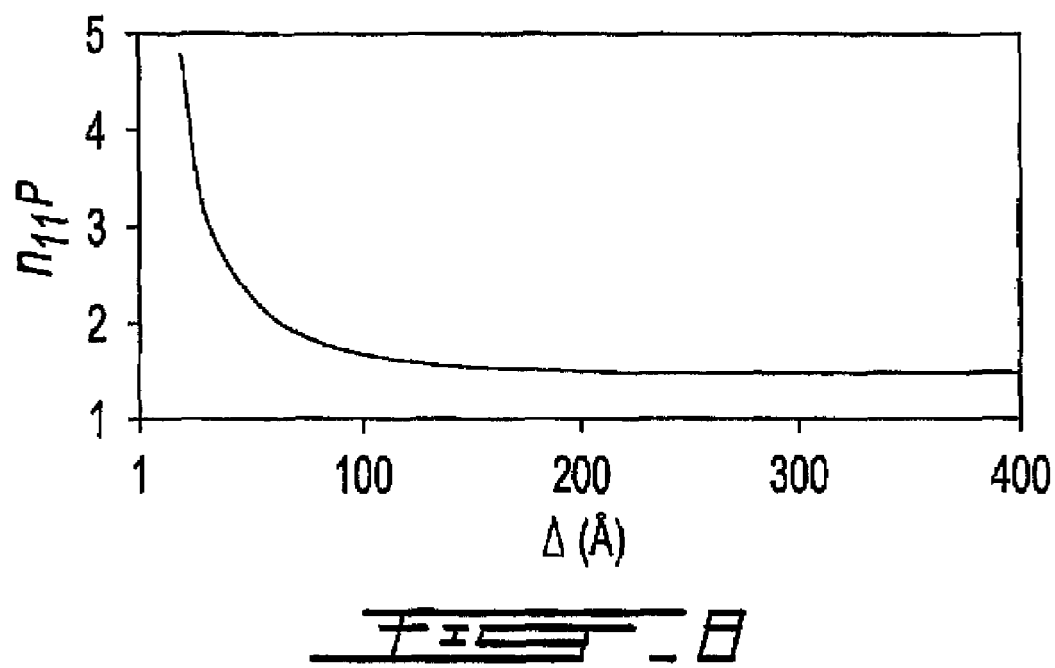
FIG. 8 is a graph showing the dependence between a normalized propagation constant $n_{11}^p$ of the SPP and a thickness $\Delta$ of the metal layer.

The dependence between the normalised propagation constant $n_{11}^p$ of the SPP 46 and the thickness Δ of the metal layer 34 is presented in FIG. 8. In contrast to the case of the WFM 40, the normalised propagation constant $n_{11}^p$ of the SPP 46 is dramatically altered with a change in the thickness Δ of the metal layer 34 between approximately 20 and 150 Å.

Figure 9:
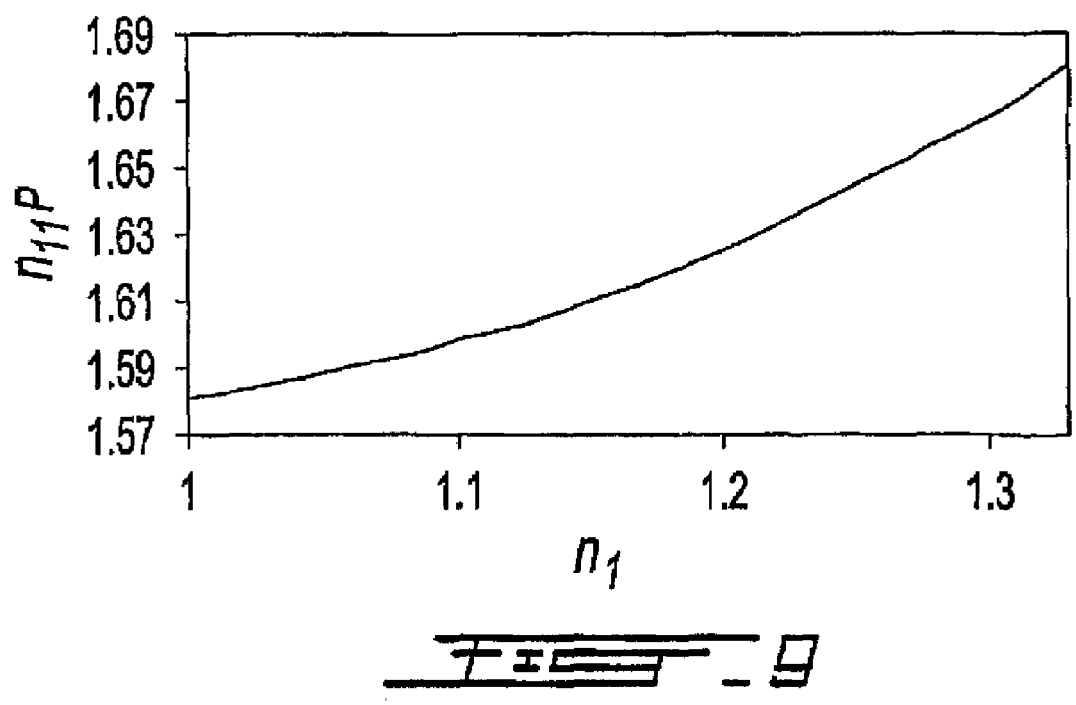
FIG. 9 is a graph showing the dependence between the normalized propagation constant $n_{11}^p$ of the SPP and a refractive index $n_1$ of a testing medium.

The normalised propagation constant $n_{11}^p$ of the SPP 46 is also very sensitive to the refractive index $n_1$ of the testing medium 32 as can be seen in FIG. 9. The normalised propagation constant $n_{11}^p$ of the SPP 46 changes by approximately 0.1 when the refractive index $n_1$ of the testing medium 32 changes by 0.33. Therefore, this makes the SPP 46 an excellent tool for sensing a change in refractive index $n_1$.

Short-period Fiber Bragg Grating (SPG)

The efficiency of the SPP 46 excitation as a function of the SPG 44 reflectivity R has been determined on the basis of well developed coupled-mode theory for fiber Bragg gratings described in details in a number of references [12-14]. There are two main conditions for achieving high efficiency of SPP 46 excitation.

The first condition is to phase-match the propagation constant of the WFM 40 with the propagation constant of the SPP 46, by properly designing the grating period Λ the SPG 44 for a predetermined wavelength of interest. This has been done in the well known case of core-cladding fiber mode coupling as described in reference [13].

The second condition is to determine the coupling constants between the WFM 40 and the SPP 46 by properly designing fiber and grating parameters of the SPG 44. For the purpose of illustration, un-tilted fiber Bragg gratings are used in one embodiment. Of course, other types of fiber Bragg gratings can be implemented as well. Using un-tilted fiber Bragg gratings, the only non-zero coupling constants are those between the WFM 40 and the SPP 46 with the same azimuth numbers as taught by reference [13]. Following the teaching of reference [13], the coupling constants between the WFM 40 and the SPP 46 are calculated using the following relation:

$$k_{11\text{-}11}^{p\text{-}f} = \frac{k_0 n_2^2 \sigma}{4Z_0} \int_0^{2\pi} d\Phi \int_{r_m}^{r_2} r\, dr (E_r^p E_r^{f*} + E_\Phi^p E_\Phi^{f*}) \quad (9)$$

where σ is the amplitude of the refractive index modulation of the SPG 44 (see reference [13]). For simplicity, σ is referred to as the grating strength. The analytical expression for $k_{11\text{-}11}^{p\text{-}f}$ is presented in the attached Appendix 1.

For designing the optimal cylindrical multi-layered optical fiber waveguide sensor 30, the influence of the different grating parameters (R, Λ, σ) and the layered structure on the grating reflectivity R is examined. The spectral location for the resonance connected with the WFM 40-SPP 46 reflection on the grating is given by:

$$\delta_{co\text{-}p} + k_{f\text{-}f}/2 = 0, \quad (10)$$

where $\delta_{co\text{-}p} = (\beta_{11}^f + \beta_{11}^p - 2\pi/\Lambda)/2$, Λ is the period of the grating, and $\beta_1^f$ and $\beta_{11}^p$ are the fiber core propagation mode and the polariton propagation constants, respectively. $k_{f\text{-}f}$ is the core-mode self-coupling constant, which is proportional to σ and is given by relation:

$$k_{f\text{-}f} = \frac{k_0 n_2^2 \sigma}{2Z_0} \int_0^{2\pi} d\Phi \int_{r_m}^{r_2} r\, dr (|E_r^f|^2 + |E_\Phi^f|^2). \quad (11)$$

The analytical expression for $k_{f\text{-}f}$ can also be found in Appendix 1.

For practical purposes, such as simplification of the production process and device miniaturization, the grating period Λ can be increased and the grating length L can be reduced. Keeping the spectral location of the WFM 40-SPP 46 reflection resonance fixed ($\lambda_{res}$=1.55 μm) and changing the grating strength σ, it is possible to change the period Λ of the grating. This dependence is presented in FIG. 10 (left axis). When the grating strength σ becomes stronger, the grating period Λ decreases slightly, as a consequence of the relationships (10) and (11). Increasing the grating strength σ increases the reflectivity R dramatically, since the WFM 40-SPP 46 coupling constant $k_{11\text{-}11}^{f\text{-}p}$, presented by equation (9) is proportional to σ (FIG. 10, right axis).

The second parameter of the grating, which influences the grating reflectivity R, is the length L of the grating. Again, increasing the grating length L increases the grating reflectivity R for a fixed grating period Λ, as illustrated in FIG. 11.

Results

In order to test the performance of the optical fiber waveguide sensor 30, the parameters of the optical fiber waveguide sensor 30 have been set as described hereinafter and telecommunication wavelengths have been used.

In order to reduce losses, the layer 34 has been made of a metal having an absolute value of the real part of the permittivity sufficiently large compared to its imaginary part at telecommunication wavelengths. The best materials from this point of view are gold and silver; gold was used in the simulations reported by reference [10]. Also, the limit of zero damping, $\Gamma \to 0$, is a good approximation for sensing applications, as plasma resonances are far away.

The WFM 40 with v=1 was considered. The radius of the testing medium was $r_1$=7 μm, the thickness Δ of the WL 36 was Δ=($r_2 - r_m$)=10 μm, the refractive index of the WL 36 was $n_2$=1.442, and the refractive index of the cladding 38 was $n_3$=1.4. The metal layer 34 was made of gold (Au).

It should be noted that in contrast to a purely dielectric fiber such as a classical fiber 100 as illustrated in FIG. 6, the WFM 40 of an optical fiber with a metal layer 34 has a hybrid nature. It consists of the WFM 40 of the multi-layered dielectric optical fiber coupled with the SPP 46 supported by the metal layer 34, oscillating in the WL 36, having maxima at the metal-dielectric boundaries $r=r_1$ and $r=r_m$, and decaying exponentially in the vicinity of these boundaries.

Figure 12A:
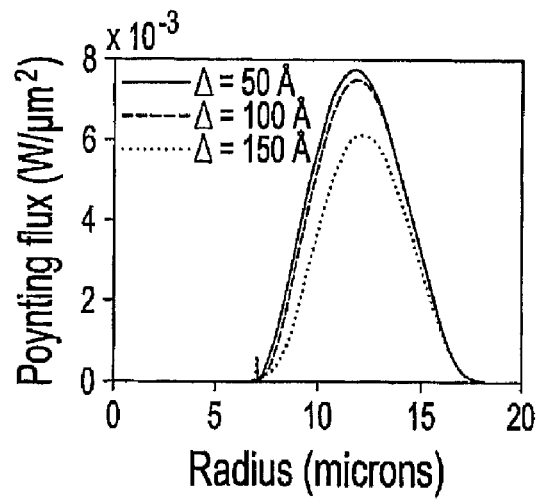
FIGS. 12a and 12b are graphs illustrating Poynting fluxes of the Waveguided Fiber Modes (WFM) versus the optical fiber radius r $\Delta$=50 Å, $\Delta$=100 Å, and $\Delta$=500 Å.
Figure 12B:
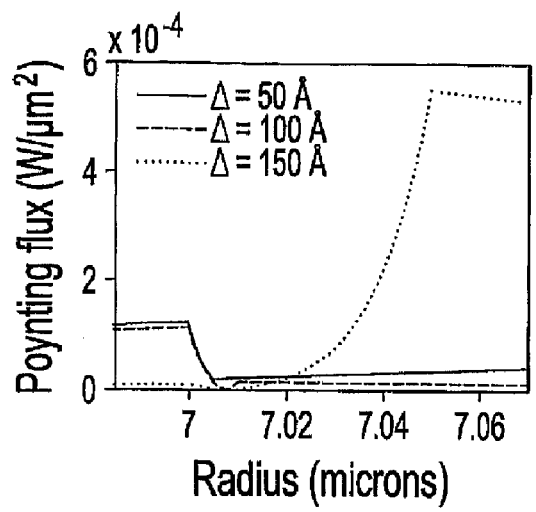

The Poynting fluxes of such a hybrid WFM 40 in optical fiber waveguide sensors 30 with different thicknesses Δ of the metal layer 34 are presented in FIGS. 12a and 12b as a function of the radius from the longitudinal axis 42. FIG. 12a shows the Poynting flux distributions throughout the layered optical fiber waveguide sensors 30; the SPPs 46 supported by the metal layers 34 coupled with the WFMs 40 can be seen. In the different multi-layered optical fiber waveguide sensors 30, the metal layer 34 is thin, more specifically having a thickness given by Δ<$\lambda_p$/2π. This means that the SPP 46 on the boundaries $r=r_1$ and $r=r_m$ are coupled with each other and form a single SPP 46 propagating along the metal layer 34.

FIG. 12(b) illustrates the Poynting flux distributions in the vicinity of the metal layer 34 for metal layer thicknesses of Δ=50 Å, Δ=100 Å, and Δ=500 Å. For a metal layer thickness of Δ=500 Å, the SPP 46 is more localized at the boundary between the WL 36 and metal layer 34 than for the other thicknesses Δ of the metal layer 34. This situation reverses as the metal layer thickness decreases (optical fiber waveguide sensors 30 with thicknesses Δ equal to 100 Å and 50 Å). The SPP 46 of the hybrid WFM 40 becomes more localized at the boundary between the metal layer and the testing medium 32.

Figure 13:
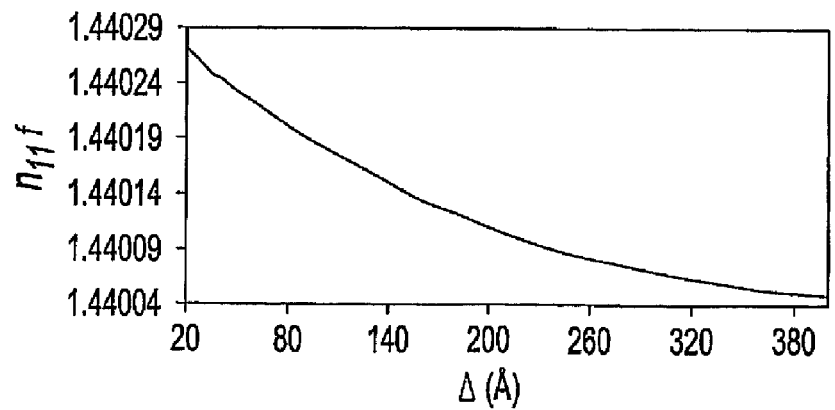
FIG. 13 is a graph showing the dependence between the WFM normalized propagation constant $n_{11}^f$ and the metal layer thickness $\Delta$.

The relation between the normalized propagation constant $n_{11}^f$ of the WFM 40 and the thickness Δ of the metal layer 34 is presented in FIG. 13. The normalized propagation constant $n_{11}^f$ is almost insensitive to the thickness Δ of the metal layer 34. It changes by about only 2×10$^{-4}$ when Δ changes by 20 times in the range of 20-400 Å.

In the process of optimizing the design of the multi-layered optical fiber waveguide sensor 30, different parameters have been changed in order to achieve the largest grating period Λ and to reduce the grating length L as much as possible while fixing the reflectivity R approximately to 70%. As it has already been mentioned, increasing the grating strength σ for a fixed or increased grating length L increases the grating reflectivity R. At the same time, the grating period Λ will also have to be slightly reduced.

For example, for σ=10$^{-4}$, the grating reflectivity R is R=16%, and the grating period is Λ=496.8 nm. For σ=5× 10$^{-4}$, the grating reflectivity R increases significantly (R=94%), and the grating period Λ remains almost unchanged (Λ=496.7 nm). In both cases the length of the gratings is L=6 cm and the thickness Δ of the metal layer 34 is Δ=100 Å. In other words, increasing the length L of the grating can increase the grating reflectivity R, but changes in the grating length L will not influence the grating period Λ at all.

In another example, for a multi-layered optical fiber waveguide sensor 30 with σ=3×10$^{-4}$, Λ=496.7 nm, and Δ=100 Å, the reflectivity R is R=16% in the case the grating length L is L=2 cm, and R=94% in the case the grating length L is L=10 cm.

It should be mentioned that the grating period Λ does change with the thickness Δ of the metal layer 34 as a consequence of the change in the normalized propagation constant $n_{11}^P$ of the SPP 46.

Figure 14:
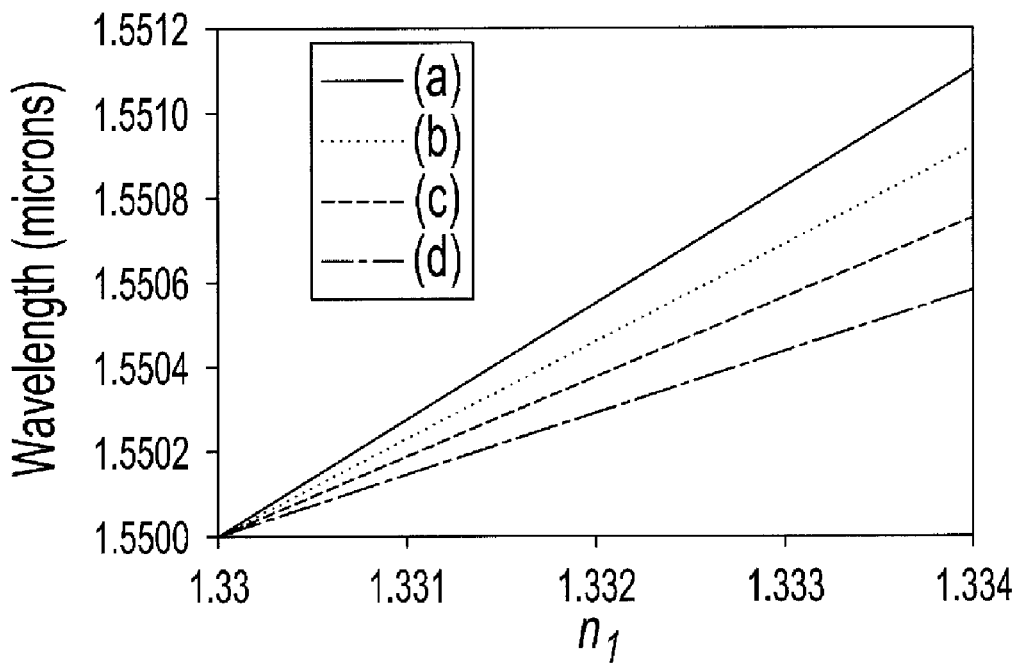
FIG. 14 is a graph of the wavelength corresponding to the maximum of the grating reflectivity R versus the refractive index $n_1$ of the surrounding medium, in which (a) L=7 cm, $\Lambda$=477 nm, $\sigma=5\times10^{-4}$, $\Delta$=80 Å, (b) L=6 cm, $\Lambda$=497 nm, $\sigma=3\times10^{-4}$, $\Delta=100$ Å, (c) L=5 cm, $\Lambda=509$ nm, $\sigma=2.3\times10^{-4}$, $\Delta=120$ Å, and (d) L=4 cm, $\Lambda=519$ nm, $\sigma=2\times10^{-4}$, $\Delta=150$ Å.

FIG. 14 illustrates the sensitivity of the multi-layered optical fiber waveguide sensor 30 by showing the relation between the refractive index $n_1$ of the testing medium 32 and the wavelength corresponding to the maximum (peak) of the grating reflectivity R. The sensitivity is presented for four different thicknesses Δ of the metal layer 34, with a equal to 80 Å, 100 Å, 120 Å, and 150 Å. By reducing the thickness Δ of the metal layer 34, essentially the sensitivity of the optical fiber waveguide sensor 30 is increased, but at the same time, in order to maintain high efficiency of the excitation of the SPP 46, the grating length L and the grating strength σ have to be increased. As a consequence, the grating period Λ only slightly changes.

For example, for a metal thickness Δ of 80 Å, the shift of the wavelength corresponding to the peak of the grating reflectivity R is approximately 280 pm per 10$^{-3}$ change in the refractive index $n_1$ of the testing medium 32. The grating reflectivity R of approximately 70% can be achieved for this thickness Δ of the metal layer 34 with a grating having the following parameters: L=7 cm, σ=5×10$^{-4}$, and Λ≈477 nm. For a metal layer 34 with a thickness Δ=100 Å, the wavelength shift of the peak of the grating reflectivity R is approximately 230 pm per the same 10$^{-3}$ change in refractive index $n_1$.

The grating reflectivity R of approximately 70% can also be realized with a grating characterized by the following parameters: L=6 cm, σ=3×10$^{-4}$, and Λ≈497 nm. For a metal layer 34 with a thickness Δ=120 Å, the wavelength shift of the peak of the grating reflectivity R is approximately 190 pm per 10$^{-3}$ change in refractive index $n_1$.

The grating reflectivity R of approximately 70% for this thickness Δ of the metal layer 34 can also be realized with a grating with L=5 cm, σ=2.3×10$^{-4}$, and Λ≈509 nm.

For a multi-layered optical fiber waveguide sensor 30 with a thickness Δ=150 Å of the metal layer 34, the wavelength shift of the peak of the grating reflectivity R is approximately 150 pm per 10$^{-3}$ change in refractive index $n_1$. The grating reflectivity R of approximately 70% for this optical fiber waveguide sensor 30 can be achieved with a grating having parameters such as L=4 cm, σ=2×10$^{-4}$, and Λ≈519 nm.

Figure 15:
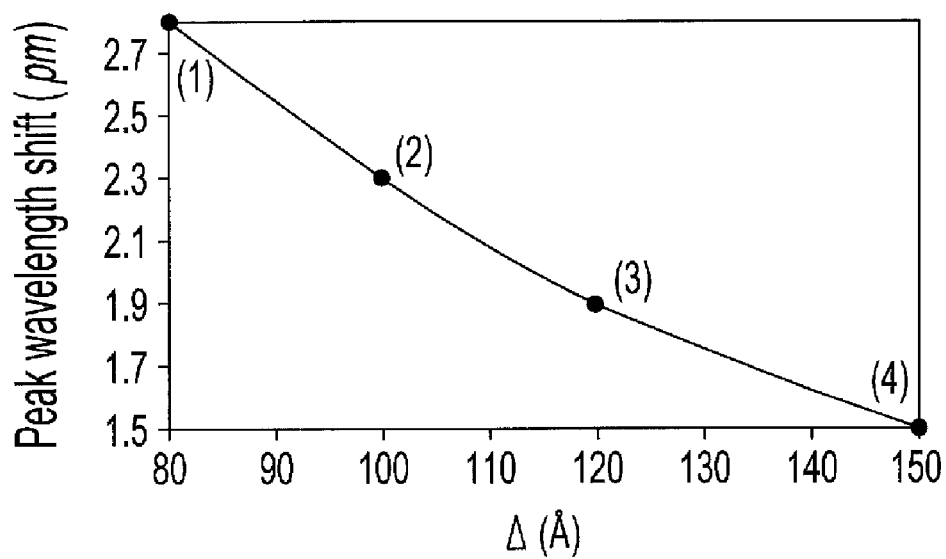
FIG. 15 is a graph of the reflectivity peak wavelength shift per $10^{-5}$ change of the refractive index $n_1$ of the surrounding medium versus the metal layer thickness $\Delta$ for four structures: (1) $\Delta=80$ Å, L=7 cm, $\Lambda=477$ nm, $\sigma=5\times10^{-4}$; (2) $\Delta=100$ Å, L=6 cm, $\Lambda=497$ nm, $\sigma=3\times10^{-4}$; (3), $\Delta=120$ Å, L=5 cm, $\Lambda=509$ nm, $\sigma=2.3\times10^{-4}$; and (4) $\Delta=150$ Å, L=4 cm, $\Lambda=519$ nm, $\sigma=2\times10^{-4}$, wherein the reflectivity R for all structures is about 70%.

The relation between wavelength shifts of the peak of the grating reflectivity R for a change of 10$^{-5}$ in refractive index $n_1$ of the testing medium 32 in the vicinity of a nominal refractive index $n_1$=1.33 (water) versus the thickness Δ of the metal layer 34 is presented in FIG. 15, for four different structures of optical fiber waveguide sensor 30. The peak wavelength shift increases from 1.5 pm to 2.8 pm per 10$^{-5}$ change in refractive index $n_1$ when the thickness Δ of the metal layer 34 decreases from 150 to 80 Å.

As a non-limitative example, the transmission of the grating can be used as an input signal for the interrogation unit (not shown) used for sensor monitoring. The interrogation unit (not shown) monitoring the transmitted WFM 40 at the output 26 of the bio-sensing set-up of FIG. 1 will then detect the shift in wavelength and by comparing the detected shift in wavelength to the shift in wavelength per 10$^{-3}$ change in the refractive index $n_s$ for a peak reflectivity R fixed at 70% and as a function of the thickness Δ of the metal layer 34, will determine the value of the refractive index $n_s$. The detected value of the refractive index $n_s$ will then be representative of detection or not of a given biological feature of the testing medium 32.

Since losses in the materials of the optical fiber waveguide sensor 30 and coupling with the radiation modes were not taken into account, the transmission of the grating can be estimated as T=100%−R. The bandwidth of the reflectivity spectrum at the first zeros is inversely proportional to the grating length L as in the case of a standard optical fiber grating for counter-propagating resonance reflection as taught by reference [13].

This example consists of estimating the sensitivity of the optical fiber waveguide sensor 30 for measuring a refractive index $n_1$ change approximately equal 10$^{-6}$ with a metal layer 32 having a thickness Δ=80 Å, a grating length L=7 cm, a grating period Λ=477 nm and a grating strength σ=5×10$^{-4}$, assuming a measurement resolution of 0.28 pm. This resolution is possible as the slope of the transmission loss spectrum edge is about 3 dB/28 pm. Assuming that a measurement in transmission of 0.01 dB can be made results in a resolution of 1 ppm in refractive index changes. It should be reminded that temperature dependence of the refractive index is a factor that must also be taken into consideration.

Figure 5:
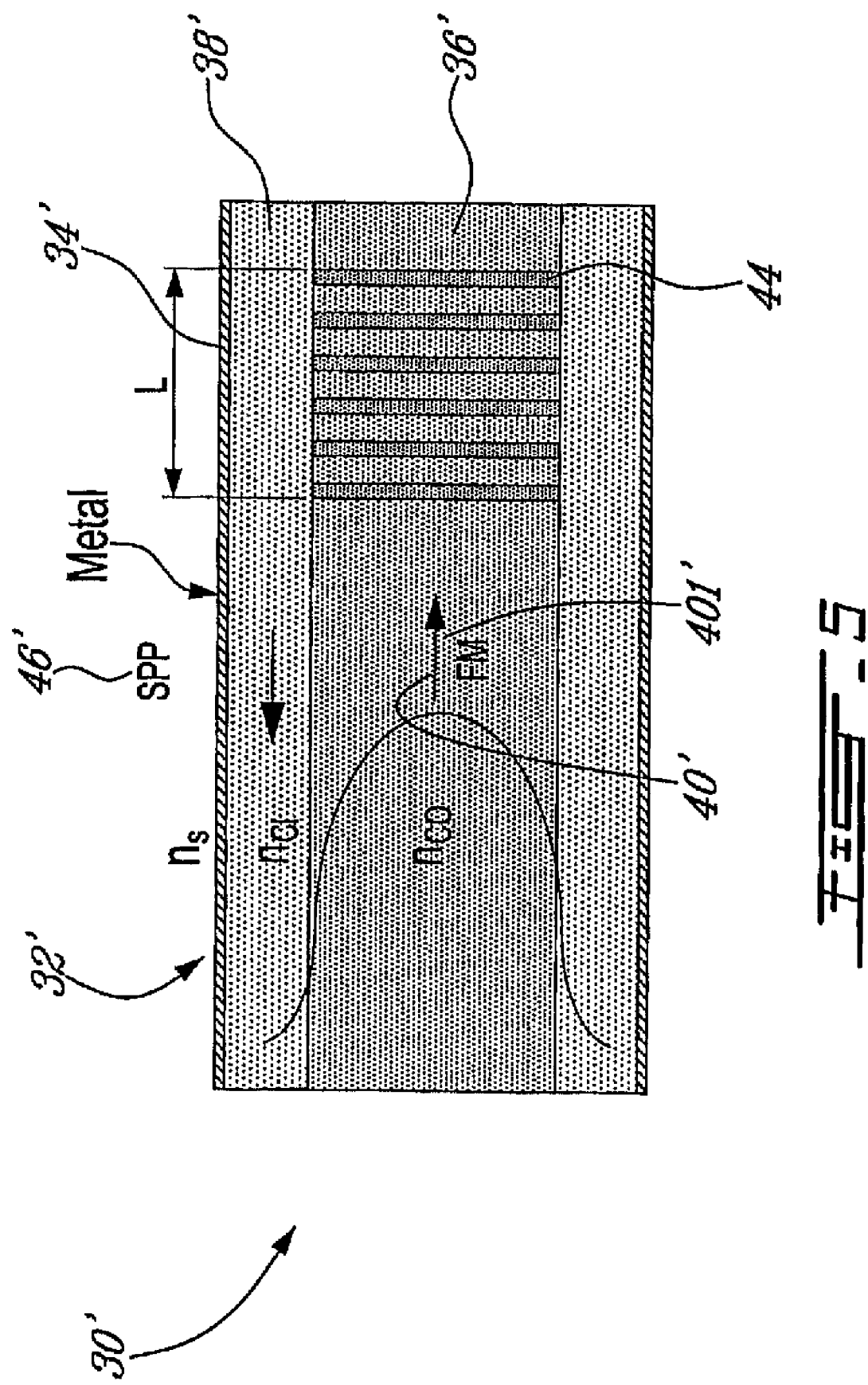
FIG. 5 is a schematic side view of an optical fiber sensor according to a third illustrative embodiment of the present invention.

FIG. 5 is a schematic side view of an optical fiber waveguide sensor 30' according to a third illustrative embodiment of the present invention. The optical fiber waveguide sensor 30' of FIG. 5 comprises a core layer 36' enclosed by a cladding layer 38'. Finally, a metal layer 34' capable of supporting a SPP 46' is deposited on the outside surface of the cladding layer 38'. The liquid 20 or other testing medium 32' is applied to the outer surface of the metal layer 34' of the optical fiber waveguide sensor 30', instead of being introduced inside the sensor as in the optical fiber waveguide sensor 30.

As shown in FIG. 5, the core layer 36' has a refractive index $n_{co}$ and allows for the core fiber mode FM 40' to be propagated in the forward direction (see arrow 401'). A SPG 44 of length L is imprinted in the core layer 36'. The cladding layer 38' has a refractive index $n_{cl}$ and the surrounding testing medium 32' has a refractive index $n_s$.

The permittivity $\in(\omega)$ of the metal layer 34' is given by the Drude formula as provided hereinabove. The theoretical aspect for the optical fiber waveguide sensor 30' is similar to the theoretical aspect for the optical fiber waveguide sensor 30. Therefore, only the differences will be discussed hereinbelow.

Using the permittivity $\in(\omega)$, the range of frequencies in which the multi-layered optical fiber waveguide sensor 30' can support the SPP 46 is determined by the condition: $\in(\omega)<-n_{cl}^2$.

As already indicated hereinabove, the field components of the SPP 46 have their maxima at the interface between the metal layer 34' and the surrounding medium 32' and at the interface between the metal layer 34' and the cladding layer 38'. The SPP 46 decays exponentially into the surrounding medium 32' and cladding layer 38'. In order to achieve a large overlap between the SPP 46 and the core fiber mode FM 40', the thickness of the cladding layer has to be very small compared to a standard single mode optical fiber.

In order to simplify the device production process, it is beneficial to essentially increase the diameter of the fiber core 36'. Despite the dramatic reduction of the thickness of the cladding layer, the overall diameter of the optical fiber waveguide sensor 30' due to the increase of the diameter of the core layer 36' allows the overall structure to be easily handled.

During testing, telecommunication wavelengths were used. The diameter of the core layer was 26 µm, the refractive index $n_{co}$ was 1.44072, and the outer diameter of the cladding layer was 30 µm, with a refractive index $n_{cl}$ of 1.44. This resulting optical fiber was a single mode fiber. The fiber core mode was used for exciting the SPP 46.

Figure 16A:
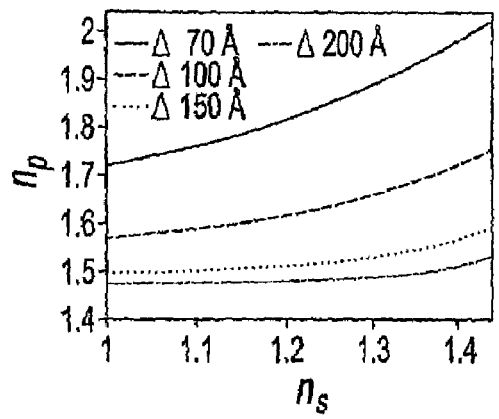
FIGS. 16a and 16b are graphs of the plasmon-polariton propagation constant $n_p$ versus the refractive index $n_s$ of the surrounding medium and the metal layer thickness $\Delta$.
Figure 16B:
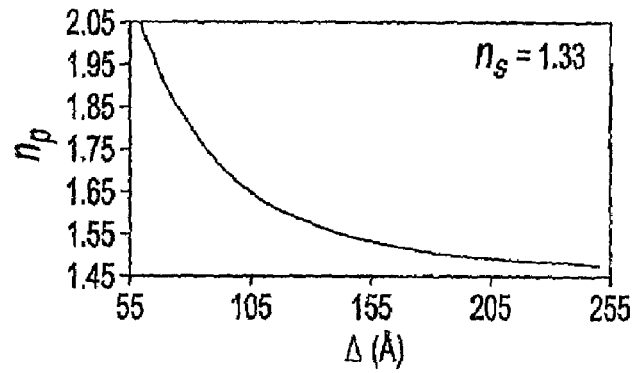

For design optimization, the relation should be understood between the SPP-FM, the parameters of the layered optical fiber waveguide sensor 30' and the grating. The value of $n_p$, corresponding to the effective refractive index of the SPP 46, is very sensitive to changes in the refractive index $n_s$ of the surrounding medium, as it can be seen in FIG. 16(*a*), and to the thickness $\Delta$ of the metal layer 34', as shown in FIG. 16(*b*).

The sensitivity of the SPP 46 to the refractive index $n_s$ is very suitable for sensor applications. As illustrated in FIG. 16(*b*), increasing the thickness $\Delta$ of the metal layer 34' decreases the value of the effective refractive index $n_p$. Changes in the geometric parameters of the structure of the optical fiber waveguide sensor 30', such as the diameter of the core layer 36' and the diameter of the cladding layer 38' do not dramatically change the parameters of the SPP 46'. These changes can quantitatively change the effective refractive index $n_p$, but cannot change the relation of the index $n_p$ with the index $n_s$ and the thickness $\Delta$.

The thickness $\Delta$ of the metal layer 34' and the refractive index $n_s$ of the surrounding medium 32' are the main factors that influence the parameters of the SPP 46 such as the effective refractive index $n_p$. However, the diameters of the core layer 36' and the cladding layer 38', the refractive indexes of the other layers as well as the grating length L and the amplitude of the refractive index modulation of the SPG 44 (grating strength $\sigma$) are other parameters that can be adjusted for optimizing the efficiency of the excitation of the SPP 46.

The grating strength $\sigma$ is a parameter that can be used for optimizing the grating period $\Lambda$, according to equation (10) given hereinbelow. At the same time, the grating length L and the grating strength $\sigma$ can also be used to optimize the grating reflectivity R.

$$\delta_{co\text{-}p} + k_{co\text{-}co}/2 = 0 \quad (10)$$

where $\delta_{co\text{-}p} = (\beta_{co} + \beta_p - 2\pi/\Lambda)/2$.

As mentioned in the foregoing description, for device miniaturization and ease of production, the grating length L should be reduced as much as possible and the grating period $\Lambda$ should be made the largest possible. By increasing the grating strength $\sigma$ for a fixed grating length L, the grating reflectivity R can be increased; this also leads to a reduction in the grating period $\Lambda$. Indeed, from equation 10, $\beta_{co}$ and $\beta_p$, the fiber core mode and polariton propagation constants, respectively, are independent from the grating strength $\sigma$, while $\kappa_{co\text{-}co}$, corresponding to the core mode self-coupling constant, is proportional to the grating strength $\sigma$. As can be seen from equation (10), the grating period $\Lambda$ is proportional to the reciprocal of the grating strength $\sigma$ and, as a consequence, it becomes smaller when the grating strength $\sigma$ is increased.

As an example, for a grating strength $\sigma = 10^{-4}$, the grating reflectivity R is R=2.3%, and the grating period is $\Lambda$=475 nm for a metal layer thickness of 100 Å. For a grating strength $\sigma = 5 \times 10^{-4}$, the grating reflectivity R increases significantly (R=55%), but the grating period $\Lambda$ reduces to 404 nm. In both cases the grating length is fixed to L=8 cm. In this example, the surrounding medium 32' is considered to be water with $n_s$=1.33, which is typical in bio-sensing applications.

Figure 17:
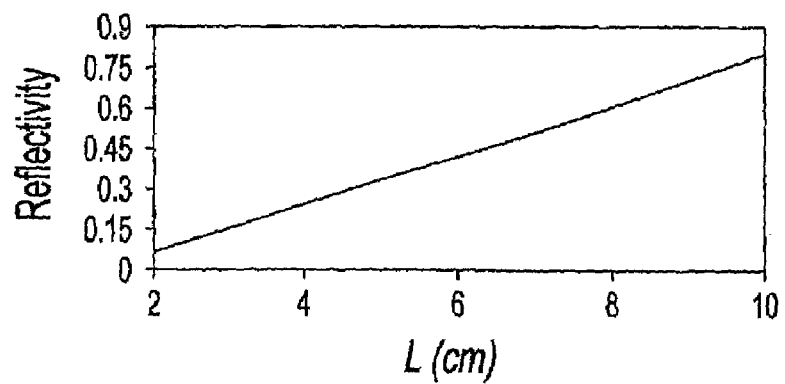
FIG. 17 is a graph showing the grating reflectivity R versus the grating length L, for $\Lambda=420$ nm, $\sigma=4\times10^{-4}$, $n_s=1.33$, and $\Delta=100$ Å.

Although increasing the grating length L increases the reflectivity R, it does not affect the grating period $\Lambda$. However, changing the grating strength $\sigma$ does affect the grating period $\Lambda$, since it affects the propagation constant $\beta_{co}$ of the guided mode because the refractive index $n_{co}$ of the core layer also changes as described in equation (10). The dependence of the grating reflectivity R on the grating length L is illustrated in FIG. 17 for a refractive index $n_s$=1.33.

FIG. 18 illustrates the relation between the wavelength corresponding to the maximum (peak) of grating reflectivity R of the multi-layered optical fiber waveguide sensor 30' and the refractive index $n_s$ of the surrounding medium 32'. The sensitivity of the fiber sensor 30' is presented for three different thicknesses $\Delta$ (100 Å, 130 Å, and 150 Å) of the metal layer 34'. Reducing the thickness $\Delta$ of the metal layer 34' essentially increases the sensitivity of the optical fiber waveguide sensor 30', but at the same time in order to maintain a high excitation efficiency of the SPP 46, the grating length L as well as the grating strength $\sigma$ are increased and, as a consequence, the grating period $\Delta$ is reduced. These results are substantially the same as in the case of the optical fiber waveguide sensor 30.

Table 1 summarizes the data used to build the graph of FIG. 18, which shows the sensitivity of the optical fiber waveguide sensor 30', i.e. the shift in wavelength per $10^{-3}$ change in the refractive index $n_s$ for a peak reflectivity R fixed at 70% and as a function of the thickness $\Delta$ of the metal layer 34'. For higher sensitivity (300 pm shift in wavelength/$10^{-3}$ change in the refractive index $n_s$), a thin metal layer 34' is required with a grating length L of 9 cm and a strong grating strength $\sigma$.

As a non-limitative example, the transmission of the grating can be used as an input signal for the interrogation unit (not shown) used for sensor monitoring. The interrogation unit (not shown) monitoring the transmitted FM 40' at the output 26 of the bio-sensing set-up of FIG. 1 will then detect the shift in wavelength and by comparing the detected shift in wavelength to the shift in wavelength per $10^{-3}$ change in the refractive index $n_s$ for a peak reflectivity R fixed at 70% and as a function of the thickness $\Delta$ of the metal layer 34', will determine the value of the refractive index $n_s$. The detected value of the refractive index $n_s$ will then be representative of detection or not of a given biologic feature of the testing medium 32'.

However, even with a short grating length L of 4 cm, it is possible to achieve a reflectivity R of 70% for a metal layer of larger thickness $\Delta$ of 150 Å, but with half the wavelength shift sensitivity (150 pm/$10^{-3}$ change in the refractive index $n_s$). It should be noted that the grating length L and the grating strength $\sigma$ inversely varies with the thickness $\Delta$ of the metal layer 34', while maintaining the reflectivity R at 70%; this is due to the increased overlap of the SPP 46 and FM 40' but this reduces the wavelength shift sensitivity to change in the refractive index $n_s$ of the surrounding medium 32'.

According to the above presented results, it is possible to estimate the sensitivity of a optical fiber waveguide sensor 30' for measuring the change in refractive index $n_s$ with a metal layer thickness $\Delta$=100 Å, a grating length of L=9 cm, a grating period $\Lambda$=420 nm, and a grating strength $\sigma$ (or GS)=$4 \times 10^{-4}$ to be approximately $10^{-6}$, assuming a measurement resolution of 0.3 pm. This resolution is possible as the slope of the edge of the transmission loss spectrum is ~3 dB/30 pm. Assuming that a change in transmission of 0.01 dB can be measured, results in a resolution of 1 ppm in refractive index change for such an optical fiber waveguide sensor 30' is possible.

An advantage of an optical fiber waveguide sensor 30' is that it can be easily exposed to the medium 32' and cleaned for use in a clinical laboratory for high volume analysis. Also, several different optical fiber waveguide sensors 30' of varying sensitivities or sensing capability (chemical type) can be integrated into one platform for parallel analysis.

Another advantage of the optical fiber waveguide sensor 30 or 30' over other sensors based on prism coupling techniques is that it comprises no moving parts, it is compact and has a high sensitivity as described in the foregoing description.

Also, the above described SPP 46 scheme compares favorably with the attenuated-total-reflection technique since it is free from moving parts to control the incident angle of the light beam. The optical fiber waveguide sensor 30 or 30' is an all fiber sensor and can be directly fusion spliced into fiber-optic systems for low insertion losses.

It should be noted that, although the present invention has been more extensively described for a cylindrical structure such as an optical fiber, it can be realized in a planar geometry as describe in FIGS. 1 and 2 without loss of generality.

Figure 19:
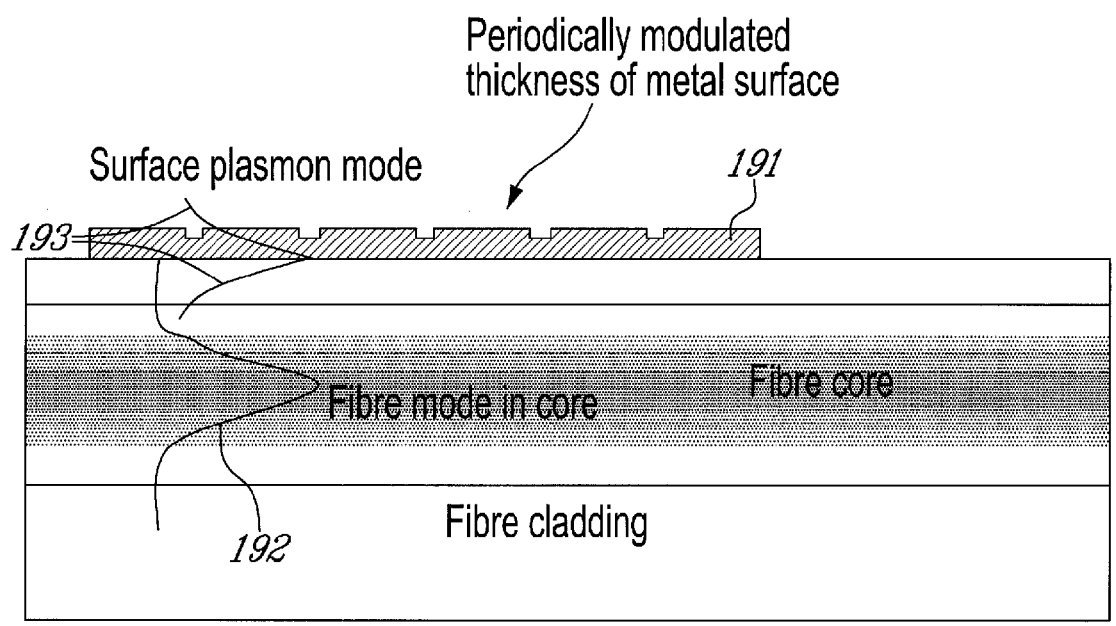
FIG. 19 is a schematic side view of an optical fiber waveguide sensor according to a further illustrative embodiment of the present invention, comprising a metal layer modulated in thickness.

Also, a surface plasmon on an optical fiber or waveguide surface may be excited by the arrangement of FIG. 19. In this particular case, the metal layer 191 is modulated in thickness, material or grade in a periodic way to allow phase matching between the guided mode such as 192 and the surface plasmon 193. The thickness, material or grade modulation can be made according to a fixed period or can be chirped.

The phase-matching condition is given by:

$$\beta_{guided\ mode}+\beta_{plasmon}+\beta_{grating}=0$$

where β refers to the phase parameter of the subscripted item. The grating phase constant is given by:

$$\beta_{grating}=2\pi/\Lambda$$

where Λ is the period of the modulation.

The thickness, material or grade modulation of the metal layer 191 presents the advantages that it can be easily fabricated, altered, manufactured, and has no moving parts. The liquid is placed on the top outer surface of the metal layer 191 for sensing the refractive index which is measured by detecting a shift in the wavelength of the resonance coupling given by the equation:

$$\beta_{guided\ mode}+\beta_{plasmon}+\beta_{grating}=0$$

Although the present invention has been described in the foregoing description by means of non-restrictive illustrative embodiments, these embodiments can be modified at will within the scope of the appended claims, without departing from the spirit and nature of the subject invention.

APPENDIX 1

In this appendix, the analytical expression for the coupling constant of the WFM-SPP described by equation (9) is presented. Using the expressions (4), (7) and (9) we have:

$$k_{11-11}^{f-p} = \frac{\pi\sigma n_2^2}{4k_0 Z_0}\tilde{u}_2\tilde{w}_2[-a^f a^p I_5 + b^f b^p I_1 + c^f c^p I_6 - d^f d^p I_2 + a^f c^p I_7 - b^f d^p I_3 - c^f a^p I_8 + d^f b^p I_4];$$

where $$a^f = C_2^f - \frac{A_2^f}{n_2^2};$$

-continued $$b^f = C_2^f + \frac{A_2^f}{n_2^2};$$

$$c^f = D_2^f - \frac{B_2^f}{n_2^2};$$

$$d^f = D_2^f + \frac{B_2^f}{n_2^2};$$

$$a^p = C_2^p - \frac{A_2^p}{n_2^2};$$

$$b^p = C_2^p + \frac{A_2^p}{n_2^2};$$

$$c^p = D_2^p - \frac{B_2^p}{n_2^2};$$

$$d^p = D_2^p + \frac{B_2^p}{n_2^2};$$

$I_i = \tilde{I}_i(\tilde{r}_2) - \tilde{I}_i(\tilde{r}_m);\ i=1, 2, 3, 4, 5, 6, 7, 8.$ $\tilde{I}_1(\tilde{r}) = \tilde{r}(\tilde{w}_2 J_0(\tilde{u}_2 \tilde{r}) I_1(\tilde{w}_2 \tilde{r}) + \tilde{u}_2 J_1(\tilde{u}_2 \tilde{r}) I_0(\tilde{w}_2 \tilde{r}))/(\tilde{u}_2^2 - \tilde{w}_2^2);$ $\tilde{I}_2(\tilde{r}) = \tilde{r}(\tilde{w}_2 J_0(\tilde{u}_2 \tilde{r}) K_1(\tilde{w}_2 \tilde{r}) + \tilde{u}_2 Y_1(\tilde{u}_2 \tilde{r}) K_0(\tilde{w}_2 \tilde{r}))/(\tilde{u}_2^2 - \tilde{w}_2^2);$ $\tilde{I}_3(\tilde{r}) = \tilde{r}(\tilde{w}_2 Y_0(\tilde{u}_2 \tilde{r}) K_1(\tilde{w}_2 \tilde{r}) + \tilde{u}_2 Y_1(\tilde{u}_2 \tilde{r}) K_0(\tilde{w}_2 \tilde{r}))/(\tilde{u}_2^2 - \tilde{w}_2^2);$ $\tilde{I}_4(\tilde{r}) = \tilde{r}(\tilde{w}_2 Y_0(\tilde{u}_2 \tilde{r}) I_1(\tilde{w}_2 \tilde{r}) + \tilde{u}_2 Y_1(\tilde{u}_2 \tilde{r}) I_0(\tilde{w}_2 \tilde{r}))/(\tilde{u}_2^2 - \tilde{w}_2^2);$ $\tilde{I}_5(\tilde{r}) = \tilde{r}(\tilde{w}_2 J_2(\tilde{u}_2 \tilde{r}) I_1(\tilde{w}_2 \tilde{r}) - \tilde{u}_2 J_1(\tilde{u}_2 \tilde{r}) I_2(\tilde{w}_2 \tilde{r}))/(\tilde{u}_2^2 - \tilde{w}_2^2);$ $\tilde{I}_6(\tilde{r}) = \tilde{r}(\tilde{w}_2 Y_2(\tilde{u}_2 \tilde{r}) K_1(\tilde{w}_2 \tilde{r}) - \tilde{u}_2 Y_1(\tilde{u}_2 \tilde{r}) K_2(\tilde{w}_2 \tilde{r}))/(\tilde{u}_2^2 - \tilde{w}_2^2);$ $\tilde{I}_7(\tilde{r}) = \tilde{r}(\tilde{w}_2 J_2(\tilde{u}_2 \tilde{r}) K_1(\tilde{w}_2 \tilde{r}) - \tilde{u}_2 J_1(\tilde{u}_2 \tilde{r}) K_2(\tilde{w}_2 \tilde{r}))/(\tilde{u}_2^2 - \tilde{w}_2^2);$ $\tilde{I}_8(\tilde{r}) = \tilde{r}(\tilde{w}_2 Y_2(\tilde{u}_2 \tilde{r}) I_1(\tilde{w}_2 \tilde{r}) - \tilde{u}_2 Y_1(\tilde{u}_2 \tilde{r}) I_2(\tilde{w}_2 \tilde{r}))/(\tilde{u}_2^2 - \tilde{w}_2^2);$ $\tilde{r} = r/k_0;\ \tilde{u}_2 = u_2/k_0,$ and $\tilde{w}_2 = w_2/k_0.$ $A_2^f, B_2^f, C_2^f, D_2^f$ correspond to the WFM, and $A_2^p, B_2^p, C_2^p, D_2^p$ correspond to the SPP.

The WFM self coupling coefficient presented by equation (10) can be found in the analytical form from the expressions (4) and (10):

$$k_{f-f} = \frac{\pi\sigma n_2^2}{2k_0 Z_0}\tilde{u}_2^2[a^{f^2}I_1^f + b^{f^2}I_2^f + c^{f^2}I_3^f + d^{f^2}I_4^f + 2a^f c^f I_5^f + 2b^f d^f I_6^f];$$

where $I_i^f = \tilde{I}_i^f(\tilde{r}_2) - \tilde{I}_i^f(\tilde{r}_m);\ i=1, 2, 3, 4.$ $\tilde{I}_1^f(\tilde{r}) = \tilde{r}^2(J_2^2(\tilde{u}_2\tilde{r}) - J_1(\tilde{u}_2\tilde{r})J_3(\tilde{u}_2\tilde{r}))/2;$ $\tilde{I}_2^f(\tilde{r}) = \tilde{r}^2(J_0^2(\tilde{u}_2\tilde{r}) + J_1^2(\tilde{u}_2\tilde{r}))/2;$ $\tilde{I}_3^f(\tilde{r}) = \tilde{r}^2(Y_2^2(\tilde{u}_2\tilde{r}) - Y_1(\tilde{u}_2\tilde{r})Y_3(\tilde{u}_2\tilde{r}))/2;$ $\tilde{I}_4^f(\tilde{r}) = \tilde{r}^2(Y_0^2(\tilde{u}_2\tilde{r}) + Y_1^2(\tilde{u}_2\tilde{r}))/2;$ $$\tilde{I}_5^f = \frac{1}{\tilde{u}_2^2} \int_{(\tilde{u}_2 \tilde{r}_m)}^{(\tilde{u}_2 \tilde{r}_2)} x\, dx (J_2(x) Y_2(x));$$

$$\tilde{I}_6^f = \frac{1}{\tilde{u}_2^2} \int_{(\tilde{u}_2 \tilde{r}_m)}^{(\tilde{u}_2 \tilde{r}_2)} x\, dx (J_0(x) Y_0(x)).$$

REFERENCES

[1]. H. Raether, *Surface Plasmons*, Springer, Berlin, 1988.
[2]. R. C. Jorgenson and S. S. Yee, "A fiber-optical chemical sensor based on surface plasmon resonance", *Sens. Actuators B.*, v. 12, pp. 213-320, 1993.
[3]. C. Ronot-Trioli, A. Trouillet, C. Veillas, A. El-Shaikh, and H. Gagnaire, "Fibre optic chemical sensor based on surface plasmon monochromatic exitation", *Anal. Chim. Acta.*, v. 319, pp. 121-127, 1996.
[4]. C. Ronot-Trioli, A. Trouillet, C. Veillas, and H. Gagnaire, "Monochromatic excitation of surface plasmon resonance in an optical-fibre refractive-index sensor", *Sens. Actuators A.*, v. 54, pp. 589-593, 1996.
[5]. W. B. Lin, N. Jaffrezic-Renault, A. Gagnaire, and H. Gagnaire, "The effects of polarization of the incident light-modeling and analysis of a SPR multimode optical fiber sensor", *Sens. Actuators A.*, v. 84, pp. 198-204, 2000.
[6]. N. A. Januts, K. S. Baghdasaryan, Kh. V. Nerkararyan, B. Hecht, "Excitation and superfocusing of surface plasmon polaritons on a silver-coated optical fiber tip", *Opt. Comm.* v. 253, pp. 118-124, 2005.
[7]. B. D. Gupta, Anuj K. Sharma, "Sensitivity evaluation of a multi-layered surface plasmon resonance-based fiber optical sensor: a theoretical study", *Sens. Actuators B.*, v. 107, pp. 40-46, 2005.
[8]. M. Iga, A. Seki, K. Watanabe, "Hetero-core structured fiber optic surface plasmon resonance sensor with silver film", *Sens. Actuators B.*, v. 101, pp 0.368-372, 2004.
[9]. A. Trouillet, C. Ronot-Trioli, C. Veillas, and H. Gagnaire, "Chemical sensing by surface plasmon resonance in a multimode optical fibre", *Pure Appl. Opt.*, v. 5, pp. 227-237, 1996.
[10]. J. Homola, S. S. Yee, and G. Gauglitz, "Surface plasmon resonance sensors: review", *Sens. Actuators B.*, v. 54, pp. 3-15, 1999.
[11]. D. Marcuse, Theory of Dielectric Optical Waveguides, (Academic Press, Inc. 1991).
[12]. H. Khosravi, D. R. Tilley, and R. Loudon, "Surface polaritons in cylindrical optical fibers", *J. Opt. Soc. Am. A*, v. 8, pp. 112-122, 1991.
[13]. T. Erdogan, "Cladding-mode resonances in short- and long-period fiber grating filters", *J. Opt. Soc. Am. A.*, v. 14, pp. 1760-1773, 1997.
[14]. T. Erdogan, "Fiber grating spectra", *J. Lightwave Technol.*, v. 15, pp. 1277-1294, 1997.
[15]. G. Nemova, and R. Kashyap, "Fiber Bragg grating assisted surface plasmon-polaritons sensor", *Opt. Lett*, (In press).

What is claimed is:

1. An optical waveguide sensing device, comprising:
a waveguide layer receiving an optical signal and propagating the optical signal in accordance with a predetermined optical waveguide propagation mode; and
a testing medium surface in communication with the waveguide layer and responsive to a testing medium modifying at least one characteristic of the propagated optical signal in relation to a given parameter of the testing medium, whereby the modified characteristic of the propagated optical signal can be measured in view of determining the given parameter of the testing medium; wherein the waveguide layer comprises a grating; the optical waveguide sensing device being a multi-layer optical waveguide sensing device comprising a metal layer for supporting SPP; the metal layer being modulated in thickness, material, or grade; and the modulation of the metal layer in one of thickness, material, and grade being periodic.

2. An optical waveguide sensing device as defined in claim 1, comprising an optical interferometer unit incorporating the waveguide layer and the testing medium surface.

3. An optical waveguide sensing device as defined in claim 1, wherein the testing medium surface comprises a surface of trenches made in the waveguide layer.

4. An optical waveguide sensing device as defined in claim 1, wherein the metal layer is applied to the waveguide layer.

5. An optical waveguide sensing device as defined in claim 1, wherein the optical waveguide sensing device presents the general configuration of a section of a multi-layer optical fiber.

6. An optical waveguide sensing device as defined in claim 5, wherein the waveguide layer is tubular and comprises inner and outer surfaces.

7. An optical waveguide sensing device as defined in claim 6, further comprising a cladding layer applied to the outer surface of the tubular waveguide layer.

8. An optical waveguide sensing device as defined in claim 5, wherein the waveguide layer is cylindrical and comprises an outer surface.

9. An optical waveguide sensing device as defined in claim 8, further comprising a cladding layer applied to the outer surface of the cylindrical waveguide layer and comprising an outer surface.

10. An optical waveguide sensing device as defined in claim 1, wherein the grating is a Bragg grating.

11. An optical waveguide sensing device as defined in claim 10, wherein the Bragg grating has a grating period, a grating strength, a grating length and a grating reflectivity.

12. An optical waveguide sensing device as defined in claim 1, wherein the given parameter of the testing medium is a refractive index of said testing medium.

13. An optical waveguide sensing device, comprising:
a waveguide layer receiving an optical signal and propagating the optical signal in accordance with a predetermined optical waveguide propagation mode; and
a testing medium surface in communication with the waveguide layer and responsive to a testing medium modifying at least one characteristic of the propagated optical signal in relation to a given parameter of the testing medium, whereby the modified characteristic of the propagated optical signal can be measured in view of determining the given parameter of the testing medium; wherein the optical waveguide sensing device presents the general configuration of a section of a multi-layer optical fiber; the waveguide layer being tubular and comprises inner and outer surfaces; and wherein the waveguide layer comprises a grating; and the optical waveguide sensing device comprises a cylindrical metal layer applied to the inner surface of the waveguide layer for supporting SPP, the cylindrical metal layer defining an inner cavity to receive the testing medium.

14. An optical waveguide sensing device as defined in claim 13, wherein the metal layer is modulated in thickness, material, or grade.

15. An optical waveguide sensing device as defined in claim 14, wherein the modulation of the metal layer in thickness, material, or grade is periodic.

16. An optical waveguide sensing device, comprising:

a waveguide layer receiving an optical signal and propagating the optical signal in accordance with a predetermined optical waveguide propagation mode; and a testing medium surface in communication with the waveguide layer and responsive to a testing medium modifying at least one characteristic of the propagated optical signal in relation to a given parameter of the testing medium, whereby the modified characteristic of the propagated optical signal can be measured in view of determining the given parameter of the testing medium;

wherein the optical waveguide sensing device presents the general configuration of a section of a multi-layer optical fiber; the waveguide layer being cylindrical and comprises an outer surface; the optical waveguide sensing device comprising a cladding layer applied to the outer surface of the cylindrical waveguide layer and comprising an outer surface, and wherein the waveguide layer comprises a grating; and the optical waveguide sensing device comprises a cylindrical metal layer applied to the outer surface of the cladding layer for supporting SPP, the cylindrical metal layer defining an outer surface for contacting the testing medium.

17. An optical waveguide sensing device as defined in claim 16, wherein the metal layer is modulated in thickness, material, or grade.

18. An optical waveguide sensing device as defined in claim 17, wherein the modulation of the metal layer in thickness, material, or grade is periodic.

19. An optical waveguide sensing device as defined in claim 1, wherein the modified characteristic of the propagated optical signal comprises a wavelength shift in said propagated optical signal.

20. An optical waveguide sensing method, comprising:

receiving an optical signal and propagating said optical signal through a waveguide layer in accordance with a predetermined optical waveguide propagation mode; and applying a testing medium to a testing medium surface in communication with the waveguide layer; and modifying at least one characteristic of the propagated optical signal in relation to a given parameter of the testing medium whereby the modified characteristic of the propagated optical signal can be measured in view of determining the given parameter of the testing medium;

wherein propagating said optical signal through the waveguide layer comprises producing a SPP supported by a metal layer; and the optical waveguide sensing method comprises periodically modulating the metal layer in thickness, material, or grade.

21. An optical waveguide sensing method as defined in claim 20, wherein applying the testing medium to the testing medium surface comprises applying the testing medium to a surface of trenches made in the waveguide layer.

22. An optical waveguide sensing method as defined in claim 20, wherein propagating said optical signal through the waveguide layer comprises propagating said optical signal though a grating.

23. An optical waveguide sensing device as defined in claim 20, wherein propagating said optical signal through the waveguide layer comprises propagating said optical signal though a core layer of a section of a multi-layer optical fiber.

24. An optical waveguide sensing method as defined in claim 22, wherein the grating is a Bragg grating.

25. An optical waveguide sensing method as defined in claim 20, wherein the given parameter of the testing medium is a refractive index of said testing medium.

26. An optical waveguide sensing method as defined in claim 20, wherein the modified characteristic of the propagated optical signal comprises a wavelength shift in said propagated optical signal.

* * * * *